(12) United States Patent
Wolfenden

(10) Patent No.: US 9,393,275 B2
(45) Date of Patent: Jul. 19, 2016

(54) PROBIOTIC FOR AMELIORATION OF COCCIDIOSIS VACCINE REACTION

(71) Applicant: Novozymes A/S, Bagsvaerd (DK)

(72) Inventor: Ross Wolfenden, Rogers, AR (US)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/417,067

(22) PCT Filed: Jul. 31, 2013

(86) PCT No.: PCT/US2013/053047
§ 371 (c)(1),
(2) Date: Jan. 23, 2015

(87) PCT Pub. No.: WO2014/022572
PCT Pub. Date: Feb. 6, 2014

(65) Prior Publication Data
US 2015/0182564 A1    Jul. 2, 2015

Related U.S. Application Data

(60) Provisional application No. 61/678,454, filed on Aug. 1, 2012.

(51) Int. Cl.
| | |
|---|---|
| A61K 39/012 | (2006.01) |
| C12Q 1/02 | (2006.01) |
| A61K 35/741 | (2015.01) |
| A61K 35/744 | (2015.01) |
| A61K 35/742 | (2015.01) |
| A61K 35/74 | (2015.01) |
| A61K 39/00 | (2006.01) |
| A61K 35/00 | (2006.01) |

(52) U.S. Cl.
CPC .............. *A61K 35/742* (2013.01); *A61K 35/74* (2013.01); *A61K 35/741* (2013.01); *A61K 35/744* (2013.01); *A61K 39/012* (2013.01); *C12Q 1/02* (2013.01); *A61K 2035/115* (2013.01); *A61K 2039/552* (2013.01)

(58) Field of Classification Search
CPC . A61K 2300/00; A61K 31/205; A61K 31/47; A61K 31/35; A61K 31/505; A61K 31/53; A61K 2039/55516; A61K 2039/521; A61K 2039/55505; A61K 2039/5555; A61K 2039/55566; A61K 2039/55577; A61K 2039/55583
See application file for complete search history.

(56) References Cited

U.S. PATENT DOCUMENTS

| | | |
|---|---|---|
| 4,335,107 A | 6/1982 | Snoeyenbos et al. |
| 4,657,762 A | 4/1987 | Mikkola et al. |
| 4,689,226 A | 8/1987 | Nurmi et al. |
| 5,401,501 A | 3/1995 | Pratt |
| 5,451,400 A | 9/1995 | Stern et al. |
| 5,612,055 A | 3/1997 | Bedford et al. |
| 5,807,546 A | 9/1998 | Stern et al. |
| 6,017,525 A | 1/2000 | Logan et al. |
| 6,110,455 A | 8/2000 | Hargis et al. |
| 6,214,335 B1 | 4/2001 | Stern et al. |
| 6,461,607 B1 | 10/2002 | Farmer |
| 6,506,389 B2 | 1/2003 | Leer et al. |
| 7,247,299 B2 | 7/2007 | Lin et al. |
| 7,700,094 B1 | 4/2010 | Nsereko et al. |
| 7,708,988 B2 | 5/2010 | Farmer |
| 7,754,469 B2 | 7/2010 | Baltzley et al. |
| 2002/0146399 A1 | 10/2002 | Raczek |
| 2003/0031659 A1 | 2/2003 | Farmer |
| 2004/0101525 A1 | 5/2004 | Lin et al. |
| 2004/0241150 A1 | 12/2004 | Hargis et al. |
| 2005/0084500 A1 | 4/2005 | Molly et al. |
| 2005/0271643 A1 | 12/2005 | Sorokulova et al. |
| 2006/0057150 A1 | 3/2006 | Kodama et al. |
| 2006/0099197 A1 | 5/2006 | Farmer |
| 2008/0044501 A1 | 2/2008 | Lee et al. |
| 2008/0057047 A1 | 3/2008 | Sas et al. |
| 2008/0171102 A1 | 7/2008 | Rehberger et al. |
| 2008/0233104 A1 | 9/2008 | Farmer |
| 2009/0257995 A1 | 10/2009 | Mochizuki |
| 2010/0074873 A1 | 3/2010 | Watson |
| 2010/0074994 A1 | 3/2010 | Harel et al. |
| 2010/0092428 A1 | 4/2010 | Schmidt et al. |
| 2010/0143417 A1 | 6/2010 | Skinner et al. |
| 2012/0225050 A1 | 9/2012 | Knight et al. |
| 2013/0136695 A1 | 5/2013 | Hargis et al. |

FOREIGN PATENT DOCUMENTS

| | | |
|---|---|---|
| CN | 101569375 | 11/2009 |
| CN | 101580799 | 11/2009 |
| EP | 2011858 | 1/2009 |
| RU | 2203947 | 5/2003 |
| WO | 8806619 | 9/1988 |
| WO | 2004044186 | 5/2004 |
| WO | 2004080200 | 9/2004 |
| WO | 2005019417 | 3/2005 |
| WO | 2010068231 | 6/2010 |
| WO | 2012009712 | 1/2012 |
| WO | 2012044984 | 4/2012 |
| WO | 2014022572 | 2/2014 |

OTHER PUBLICATIONS

Stringfellow et al Poultry Science (2011) 90 (8):1652-1658.*
Klein 2009 (Thesis submitted for Master of Science).*
USPTO; Restriction Requirement dated Aug. 19, 2013 in U.S. Appl. No. 13/810,549.

(Continued)

*Primary Examiner* — Padma V Baskar
(74) *Attorney, Agent, or Firm* — Elias Lambiris

(57) ABSTRACT

Methods for improving the health of agricultural poultry are provided. For example, methods including selecting specific bacteria to form a probiotic for the administration with coccidiosis vaccines for the reduction of adverse effects associated with the coccidiosis vaccines are disclosed. In accordance with various aspects of the present disclosure, a bacterial isolate, probiotic and or treatment may be obtained by novel screening methods resulting in products that are advantageously administered with or about the same time as a coccidiosis vaccine.

18 Claims, 16 Drawing Sheets

(56) References Cited

OTHER PUBLICATIONS

USPTO; Non-Final Office Action dated Dec. 31, 2013 in U.S. Appl. No. 13/810,549.
USPTO; Non-Final Office Action dated Jun. 27, 2014 in U.S. Appl. No. 13/810,549.
USPTO; Notice of Allowance dated Jan. 30, 2015 in U.S. Appl. No. 13/810,549.
PCT; International Search Report and Written Opinion dated Mar. 14, 2012 in Application No. PCT/US2011/044326.
PCT; International Search Report and Written Opinion dated Dec. 20, 2013 in Application No. PCT/US2013/053047.
PCT; Extended European Search Report issued in European Application No. 11807617.3 on Mar. 6, 2014.
Abdollahi, M.R. et al., "Effect of different levels of bacterial probiotic on broilers performance," Animal Science Department, College of Agriculture, University of Tehran, Karaj-lran, (2003).
Alexopoulos, C. et al., "Field evaluation of the effect of a probiotic-containing Bacillus licheniformis and Bacillus subtilis spores on the health status, performance, and carcass quality of grower and finisher pigs," Journal of Veterinary Medicine Series A Physiol. Pathol. Clin. Med., 51, pp. 306-312, (2004).
Alexopoulos, C. et al., "Field evaluation of the efficacy of a probiotic containing Bacillus licheniformis and Bacillus subtilis spores, on the health status and performance of sows and their litters," Journal of Animal Physiology and Animal Nutrition, 88, pp. 381-392, (2004).
Corcionivoschi, N. et al., "The effect of probiotics on animal health," Scientific Papers: Animal Science and Biotechnologies, 43, pp. 35-41, (2010).
Hong, H.A et al., "The use of bacterial spore formers as probiotics," FEMS Microbiol. Rev., 29, pp. 813-835, (2005).
Kowalski, Z.M. et al., "Performance of Holstein calves fed milk-replacer and starter mixture supplemented with probiotic feed additive," Journal of Animal and Feed Sciences, 18, pp. 399-411, (2009).
Kritas, S.K. et al., "Effect of Bacillus licheniformis and Bacillus subtilis supplementation of ewe's feed on sheep milk production and young lamb mortality," Journal of Veterinary Medicine Series A Physiol. Pathol. Clin. Med., 53, pp. 170-173, (2006).
Link, R. et al., "Composition of sow's milk and selected metabolic indices after administration of probiotics," Research in Pig Breeding, 1, pp. 40-42, (2007).
Mahdavl, A.H. et al., "Effect of probiotic supplements on egg quality and laying hen's performance," International Journal of Poultry Science, 4, pp. 488-492, (2005).
Mahdavi, A.H. et al., "Effect of probiotic inclusion in different levels of barley substitution tor corn diets on egg quality and laying hen's performance," Pakistani Journal of Biological Sciences, 8, pp. 1521-1528, (2005).
Min et al., "Application of biotechnological tools for coccidia vaccine development—Review," J. Vet. Sci., 5, pp. 279-288, (2004).
Mutus, R. et al., "The effect of dietary probiotic on tibial bone characteristics and strength in broilers," Poultry Science, 85, pp. 1621-1625, (2006).
Oviedo-Rondón., "Molecular methods to evaluate effects of feed additives and nutrients in poultry gut microflora," R. Bras. Zootec., 38, pp. 209-225, (2009).
Pelicano, E.R.L. et al., "Effect of different probiotics on broiler carcass and meat quality," Brazilian Journal of Poultry Science, 5, pp. 207-214, (2003).
Sabatkova, J. et al., "The probiotic BioPlus 2B as an alternative to antibiotics in diets for broiler chickens," Acta Vet, BRNO, 77, pp. 569-574, (2008).
Stringfellow, K., et al., "Evaluation of Probiotic Administration on the Immune Response of Coccidiosis-Vaccinated Broilers," Poultry Science, vol. 90, pp. 1652-1658 (2011).
Wolfenden, R.E., "Evaluation of selected antibiotic alternatives for control of enteric bacterial pathogens of commercial poultry," ProQuest Dissertations & Theses: The Sciences and Engineering Collection, (2010).
Wolfenden. R.E., "Evaluation of a screening and selection method for Bacillus isolates for use as effective direct-fed microbials in commercial poultry," International Journal of Poultry Science, 9, pp. 317-323, (2010).
Zhu et al., "Improvement of the antioxidant activity of Chinese traditional fermented okara (*Meitauza*) using Bacillus subtilis B2," Food Control, 19, pp. 654-661, (2008).
EPO; European Office Action dated Jun. 19, 2015 in Application No. 11807617.3.

\* cited by examiner

B. Advent

A. Advent+PC1

B. Advent

A. Advent+PC1

PROBIOTIC FOR AMELIORATION OF COCCIDIOSIS VACCINE REACTION

FIELD OF INVENTION

The present disclosure relates in general to methods for improving the health of agricultural poultry. In particular, the present disclosure relates to the selection, formulation, and administration of treatments selected for administration with coccidiosis vaccines to mitigate certain unwanted or adverse effects following administration of coccidiosis vaccines.

BACKGROUND OF THE INVENTION

A poultry disease known as coccidiosis (also referred to as coccidia, or cocci) is caused by the parasite *Eimeria*. The various different species of *Eimeria* that specifically effect poultry include at least *Eimeria tenella, Eimeria maxima, Eimeria acervulina, Eimeria mivati, Eimeria mitis, Eimeria brunetti, Eimeria necatrix, Eimeria meleagrimitis, Eimeria adenoeides*, and *Eimeria gallopovonisl*. Coccidiosis causes a range of problems in poultry resulting in mortality, poor weight gains, poor feed conversion ratios (e.g. as measured by [total body weight gain]/[total feed consumed]), etc. The disease is addressed in commercial poultry with a variety of treatments including antibiotics and vaccines. The use of antibiotics in animal agriculture, in particular poultry production, is under increasing pressure from both consumers and government regulatory agencies. Thus, vaccines are becoming a common method of addressing coccidiosis in commercial poultry operations.

Vaccines are given to poultry to generate an appropriate immune response against *Eimeria* species. However, the use of vaccines in a semi-controlled dose of one or more fully virulent or attenuated *Eimeria* species as typically given to young poultry may result in a mild case of coccidiosis. Although mild, this still presents negative side effects in the poultry, which is displayed by a reduction in various production parameters in the poultry while they overcome the infection and create natural immunities to *Eimeria species*. Animal welfare and economically important disruptions result. For example, this decrease in production parameters translates into lost incomes when the birds are sent to market, especially in broiler birds where life cycle is short. In severe cases, adverse effects following coccidiosis vaccination requires treatment with anti-coccidial therapeutics. In other cases, an antibiotic is needed to control the secondary bacterial infection that often occurs post vaccination. A recovery from losses in these birds is generally believed to be impractical. While the use of vaccines may be an environmentally sound solution and alleviate some consumer concerns, it has substantial economic shortcomings.

SUMMARY OF THE INVENTION

In accordance with various aspects of the present disclosure, a bacterial isolate, probiotic and/or treatment may be obtained by novel screening methods resulting in products that are advantageously administered with or about the same time as a coccidiosis vaccine. In various embodiments, a method for reducing adverse effects following a coccidiosis vaccine in poultry may comprise administering a bacterium to poultry about the same time as administration of a coccidiosis vaccine. The bacterium may be selected to be from the group of bacteria collectively known as lactic acid bacteria. The bacterium may be selected from the gastrointestinal tract (GI tract) of poultry. Treatment with the bacterium may be administered in a food source, water, by oral gavage, with an edible substrate (e.g. a gel), or by aerosol spray.

In accordance with various aspects of the present disclosure, a bacterium may reduce inflammation associated with coccidiosis vaccination and/or the resulting secondary bacterial infection in poultry. The bacterium may be specifically selected to reduce the severity or presence of inflammation. Selection methods may include identification of pro-inflammatory bio-markers and monitoring reductions in these bio-markers as indicators of inflammation or immune response in the poultry. The bio-marker may be an alpha-1 glycoprotein or other inflammatory or pro-inflammatory markers.

In accordance with various aspects of the present disclosure, a specifically selected bacterium may improve food passage time. Selection methods may include identification of bio-markers and monitoring reductions in these bio-markers as indicators of food passage in the poultry. The bio-marker may be titanium dioxide.

In various embodiments, the bacterium may be selected to reduce the growth of a bacterial pathogen which causes a secondary infection associated with coccidiosis. The bacterial pathogen may be *Clostridium perfringens* or *Escherichia coli*. The bacterium may be co-administered with the coccidiosis vaccine. In various embodiments, the bacterium may not substantially modulate the immune response associated with the coccidiosis vaccine.

As several bacteria may be selected through the various methods, one or more of these selected bacteria may be combined in a pharmaceutical composition. A treatment may comprise the probiotic and at least one or more commercially available coccidiosis vaccines.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures, wherein like numerals denote like elements.

FIG. 5 illustrates body weight measurements of chicks in Experiment 1. Saline control (Neg Con), ADVENT® coccidiosis vaccine (Advent), ADVENT® coccidiosis vaccine and FLORASTART® (Advent+FS), ADVENT® coccidiosis vaccine and probiotic candidate 1 (Advent +PC1), ADVENT® coccidiosis vaccine and probiotic candidate 2(Advent+PC2), ADVENT® coccidiosis vaccine and probiotic candidate 3 (Advent +PC3), ADVENT® coccidiosis vaccine and probiotic candidate 4 (Advent +PC4), ADVENT® coccidiosis vaccine and probiotic candidate 5 (Advent +PC5). FIG. 5c, "ab" denotes not statistically different from either group "a" or group "b".

FIG. 8A illustrates treatment with ADVENT® coccidiosis vaccine and probiotic candidate 1 (Advent+PC1). FIG. 8B illustrates treatment with ADVENT® coccidiosis vaccine (Advent).

FIG. 9A illustrates treatment with ADVENT® coccidiosis vaccine and probiotic candidate 1 (Advent+PC1). FIG. 9B illustrates treatment with ADVENT® coccidiosis vaccine (Advent).

FIG. 11 illustrates body weight measurements in Experiment 4, of chicks post-treatment with saline control (Neg Con), ADVENT® coccidiosis vaccine (Advent), and ADVENT® coccidiosis vaccine and probiotic candidate 1 (Advent+PC1).

DETAILED DESCRIPTION

Figure 1:
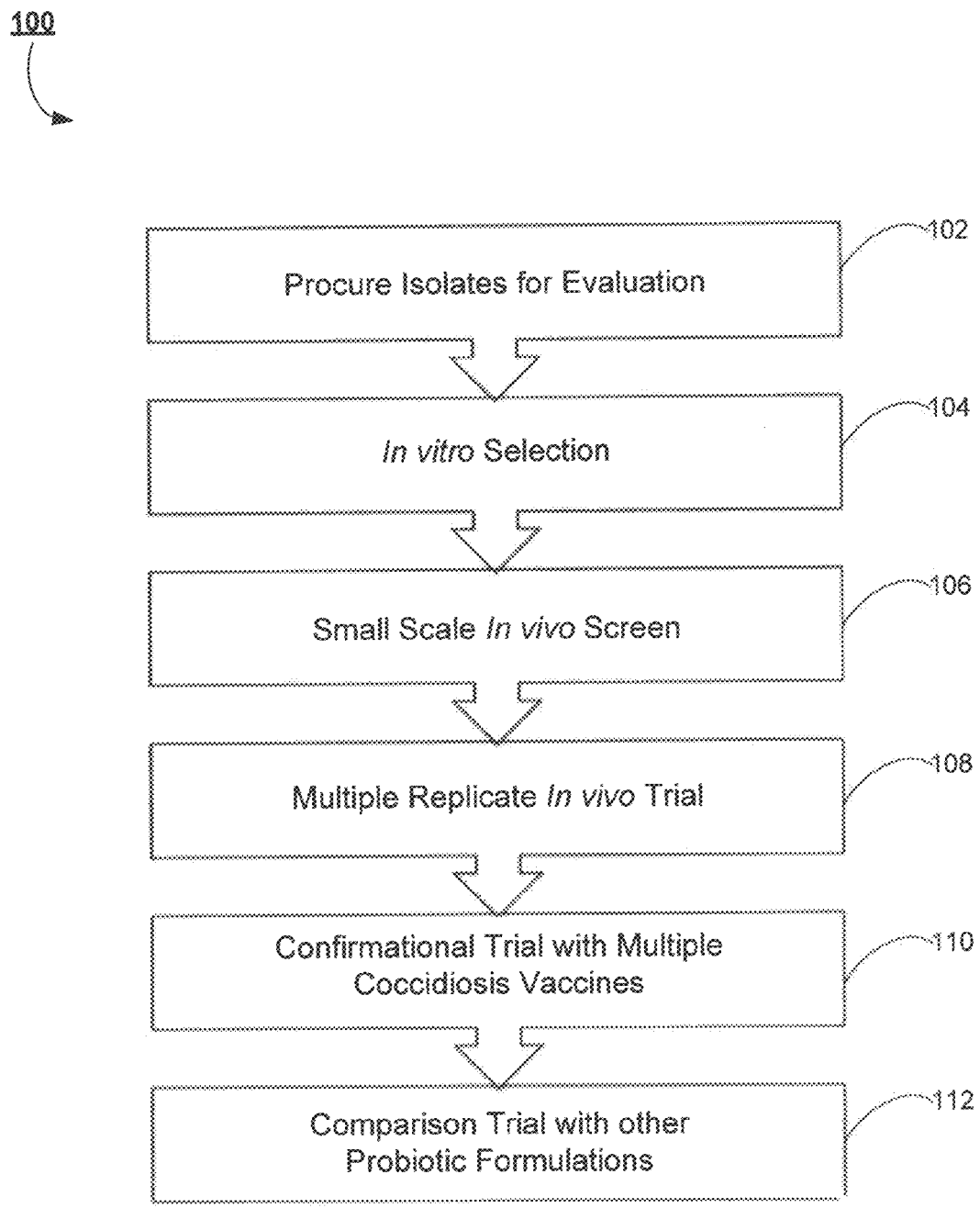
FIG. 1 illustrates a selection process flow chart in accordance with various embodiments.

The detailed description of exemplary embodiments herein makes reference to the accompanying drawings, which show exemplary embodiments by way of illustration. While these exemplary embodiments are described in sufficient detail to enable those skilled in the art to practice the inventions, it should be understood that other embodiments may be realized and that logical, chemical and mechanical changes may be made without departing from the spirit and scope of the inventions. Thus, the detailed description herein is presented for purposes of illustration only and not of limitation. For example, the steps recited in any of the method or process descriptions may be executed in any order and are not necessarily limited to the order presented. Furthermore, any reference to singular includes plural embodiments, and any reference to more than one component or step may include a singular embodiment or step.

The present disclosure may be described herein in terms of various bacterial isolates, components, compositions, treatments, screening methods, administration methods and process steps. For example, the present disclosure may employ a single isolate or combination of isolates, the composition of which may be suitably configured for various intended purposes. The various isolates, consumable products, methods of administration and methods of isolation explained herein are merely for exemplary purposes, as the disclosure can be applied to any similar application.

As used herein, the term "isolate" may mean a selected bacterial strain in a pure or uncombined state, whether present in a medium or not, that has been tested for desired attributes, criteria and or characteristics.

As used herein, the term "adverse effect" following a vaccination may include any negative, deleterious, or unwanted side effects from administration of the vaccine. A side effect may include any physiological response or effect on the recipient of the vaccine other than acquiring immunity to the targeted infectious disease of the vaccine.

As used herein, the term "poultry" may refer to one bird or a group of birds of any type of domesticated birds typically kept for egg and/or meat production. For example, poultry includes members of the order Galliformes (including chickens and turkeys) and the family Anatidae (including various ducks and geese).

As used herein, the term "administration" may mean the act of giving a vaccination or probiotic through any available means.

As used herein, the term "probiotic" may mean one or more beneficial bacterium/bacteria and/or isolates of the same that provide a therapeutic benefit to the recipient. The term "probiotic" may also include a bacterium or bacteria and/or excipients in a medium, carrier, or other vehicle suitable for use in poultry.

As used herein, the term "bio-marker" may mean a measurable biological characteristic, status, and/or other physical property or state of poultry.

As used herein, the term "selection criterion" which also may be referred to as a "criterion" or "criteria" (plural), may mean one or more values that a criterion may be assigned that indicates a tendency to reduce and/or prevent an adverse effect upon administration of both a probiotic in accordance with various embodiments and a coccidiosis vaccine.

As used herein, the term "pharmaceutical composition" means a substance (including a mixture or compound of substances) for therapeutic use, diagnosis, mitigation, treatment, cure, therapeutic benefit or prevention of disease in humans or in other animals.

As used herein, "significantly different" means statistically different. All statistical reporting in the Figures and Examples section is based on ANOVA (Analysis of Variance) modeling, as conducted through the SAS software program (SAS Institute, Inc., Cary NC) using the GLM procedure. Statistical significance was assigned to p values less than or equal to 0.05. For example, with respect to Experiment 1 data as illustrated in FIG. 5, while each of the group "a" results are numerically different, they are not considered statistically different. However, group "a" results are statistically significant from group "b" results as well as group "c" results, etc., and whereas a>b>c from both a numeric and statistical standpoint.

In accordance with various aspects of the present disclosure, an adverse effect following a coccidiosis vaccine used in poultry may be mitigated by administering a probiotic with the coccidiosis vaccine. By mitigating the adverse effect following the coccidiosis vaccine, the probiotic may allow for improved development of the poultry prior to slaughter. The probiotic may comprise one or more beneficial bacterium. While many embodiments and examples herein may include a single bacterium it is also understood that each embodiment, example, process, treatment, test, composition etc. may also include multiple bacteria.

In accordance with various aspects of the present disclosure, a pharmaceutical composition may be prepared to treat poultry that is administered a coccidiosis vaccine. Such compositions may include bacterium, bacteria, probiotic, and/or treatment formulations that may be specifically selected for one or more specific criteria which are beneficial in reducing the damage from an adverse effect following the coccidiosis vaccine. Such compositions may include at least one pharmaceutically acceptable excipient. The term "excipients," as used herein, refer to non-API substances such as carriers, solvents, lubricants and others used in formulating pharmaceutical products. Excipients are generally safe for administering to animals or humans according to established government standards, including those promulgated by the United States Food and Drug Administration. For example, the composition may include excipients such as fructooligosaccharides, inulin, lactose, dry skim milk powder, vaccine stabilizers, or various chlorine eliminators among other potential excipients.

In accordance with various aspects of the present disclosure, a selected bacterium may be characterized by the bacterium's ameliorative and/or preventative effects on adverse effects following administration of a coccidiosis vaccine. The vaccine may include any one or more suitable coccidiosis vaccines. For example, commercially available coccidiosis vaccines including but not limited to Merck Animal Health's Coccivac B, Merck Animal Health's Coccivac D2, Merck's Animal Health Paracox—5, Merck's Animal Health Paracox—8, Immucox for Chickens 1, Immucox for Chickens 2, Novus International's Advent, Merial's Hatchpak Cocci III, Pfizer Animal Health's Innovocox, Pfizer Animal Health's Innovocox EM1, and/or any other similar vaccine. Adverse effects following administration of these vaccines may include one or more adverse effects including, but not limited to, inflammation of the GI tract, GI tract lesions, changes in intestinal morphology, secondary bacterial infections in the GI tract, decrease in absorptive capacity in the GI tract, increased feed passage time, decreased body weight gain in the poultry, decreased feed efficiency during the early development stages, poultry morbidity and mortality, and decreased flock uniformity. Improvement in any of these reactions qualifies as a criterion for selection mentioned above.

In accordance with various embodiments of the present disclosure, the bacterium may be selected from a variety of lactic acid bacteria. The source of these lactic acid bacteria may be commercial, from a proprietary library strain isolated previously, or they may be environmental (i.e., a part of the poultry's environment). For example, commercially available lactic acid bacteria may be selected and cultured for further screening against other criteria. In another example, various lactic acid bacteria may be selected directly from poultry and/or poultry waste. The use of lactic acid bacteria may benefit the poultry by normalizing gut health and enabling superior flock performance independent of the benefits of reducing coccidiosis pathology. Lactic acid bacteria generally comprise a group of Gram positive, acid tolerant bacteria.

In accordance with various embodiments, the bacterium may be selected from the GI tract of the poultry. As more than one bacterium may be combined in a probiotic formulation, different bacteria from different portions of the GI tract of the poultry may be incorporated in the probiotic formulation. Different species of *Eimeria* that cause coccidiosis infect and/or reside in different parts of the GI tract of poultry and cause damage to different areas of the GI tract. In accordance with various embodiments, bacterium may be selected from specific regions of the GI tract that are most effected by the various species of *Eimeria*. Accordingly, the bacteria making up a probiotic formulation is selected to produce localized effects to the areas of the GI tract most affected by clinical and subclinical coccidiosis caused by the vaccine strain of *Eimeria*. For example, bacteria may be selected from the duodenum of poultry. In another example, bacteria may be selected from the cecum of poultry. In another example, bacteria may be selected from the ileum of poultry. In another example, bacteria may be selected from any location of the GI tract of poultry. Each bacterium selected from the duodenum, cecum, ileum, or other portion of the GI tract may be further tested to ensure that the bacterium mitigates the negative reactions of coccidiosis or the adverse effects following the coccidiosis vaccine. Bacteria may be individually selected based on an improvement of any one or more criteria discussed herein, and also based on particular improvement in a specific area of the GI tract of the poultry. For example, a bacterium may be selected for improving the lesion score in the duodenum. Notably, the selection can occur based on any portion of the GI tract in the context of any one or more criteria.

In accordance with various embodiments, the probiotic formulation may be co-administered to poultry with the coccidiosis vaccine. Co-administration of the probiotic and the coccidiosis vaccine may include administering the probiotic to poultry (and/or pharmaceutical composition) at about the same time as the coccidiosis vaccine. The phrase "about the same time" may be defined as administration that is separated by no gap in time to an identifiable but small gap in time. For example, co-administration may mean simultaneous administration, 1 second between administrations, 10 seconds between administrations, 1 minute between administrations, 10 minutes between administrations, 1 hour between administrations, 10 hours between administrations, and/or 1 day between administrations. Co-administering the coccidiosis vaccine and the probiotic formulation may include administering the two in the same pharmaceutical composition. For example, the pharmaceutical composition may comprise the probiotic and a coccidiosis vaccine. In accordance with one embodiment of the invention, the probiotic may be separately administered from the coccidiosis vaccine to poultry. Separate administration is defined as exceeding 1 or more days between administration of the probiotic and of the coccidiosis vaccine. In one example, the coccidiosis vaccine and the probiotic are administered on the day of age of the poultry. In various embodiments, the probiotic may be administered to poultry separately such as from 1-3 days apart. Certain coccidiosis vaccines are given in ovo and the probiotic may not be provided until day of age of the poultry. As such, several days may laps between vaccination and probiotic treatment.

In various embodiments, the probiotic may be administered to poultry in a second dose subsequent to the first dose. For example, the second dose may be administered between 7-21 days post vaccination. In various embodiments, the probiotic may be administered to poultry prior to administration of the coccidiosis vaccine. For example, the probiotic may be administered one or more days before the coccidiosis vaccine.

While much of the disclosure herein is directed to selection of one or more bacterium to be combined into a useful probiotic and treatment, each selection may be done at the bacterium, probiotic, and/or treatment level. For example, a single probiotic may not have the characteristics of improving a criterion but a combination of several bacteria in the probiotic composition may improve at least one criterion if not more. Similarly, various compositions in the treatment including the probiotic may possess characteristics that may improve one or more criteria.

In various embodiments, the bacterium may be selected by measuring the presence of certain bio-markers in the poultry. An increase, decrease, presence or absence of certain bio-markers may specifically indicate the presence or absence of a desirable characteristic in the bacterium. For example, a desirable bacterium may reduce a certain criterion in the poultry. A bio-marker may be used to indicate the improvement of that criterion. By analyzing the bio-marker a determination is made on whether the bacterium possesses the desired characteristic. A positive response from the bio-marker may indicate that the bacterium should be selected. In various embodiments, a negative response from the bio-marker may indicate that the bacterium should be discarded.

In accordance with various embodiments, a bacterium may be characterized by its effect of reducing the inflammation associated with a coccidiosis vaccine in the GI tract of poultry. In one example, the bacterium may be selected in response to the bacterium causing a decrease in the presence of a bio-marker that is associated with inflammation in the GI tract of poultry. The selection may be accomplished by comparing a group of poultry treated with the vaccine and the bacterium to a group of poultry only treated with the vaccine and then measuring the same bio-marker in both groups. A decrease in the bio-marker in the poultry having both the vaccine and the bacterium may indicate that the bacterium should be selected as having the desirable anti-inflammatory characteristic (i.e., a decrease in the presence of an inflammatory or pro-inflammatory related bio-marker is a positive response in this type of bio-marker). For example, a significant decrease in the presence of a bio-marker may refer to a reduction by half. But it may also be noted that the rate the bio-marker will be detected will vary from test to test depending on the severity of the challenge. Bio-markers indicative of inflammatory response in poultry may include for example, alpha-1 glycoproteins, serum ovotransferrin, C-reactive proteins, acute phase proteins, heterophil infiltration/recruitment, histamine, IL-8, nitric oxide, IL-1, tumor necrosis factor alpha, interferon gamma, etc. Additionally, bio-markers to measure gut barrier function may also be used.

In accordance with various embodiments, a bacterium may be characterized by its effect of increasing food absorption in poultry during the period the poultry is experiencing an adverse effect due to a coccidiosis vaccine. Stated another way, a bacterium may be characterized by its effect of decreasing the reduction of food absorption in poultry suffering from the negative effects of a coccidiosis vaccine. The bacterium may be selected by identifying those bacterium demonstrating a positive response on the time of food passage through the GI tract of poultry. The selection may be accomplished by obtaining a first group of poultry treated with the vaccine plus the bacterium and a second group of poultry treated only with the vaccine. The marker is administered to both the first and second group and the time it takes for the marker to pass through the gut (the "residence time") is assessed. The marker may be selected from suitable indigestible compounds. An extended or increased passage time of the marker through the poultry may indicate improved food absorption. Conversely, a decrease in passage time may indicate reduced food absorption (e.g. in poultry having digestive stress). Suitable markers may include, for example, titanium dioxide, chromium dioxide, ferric oxide, etc.

Figure 2:
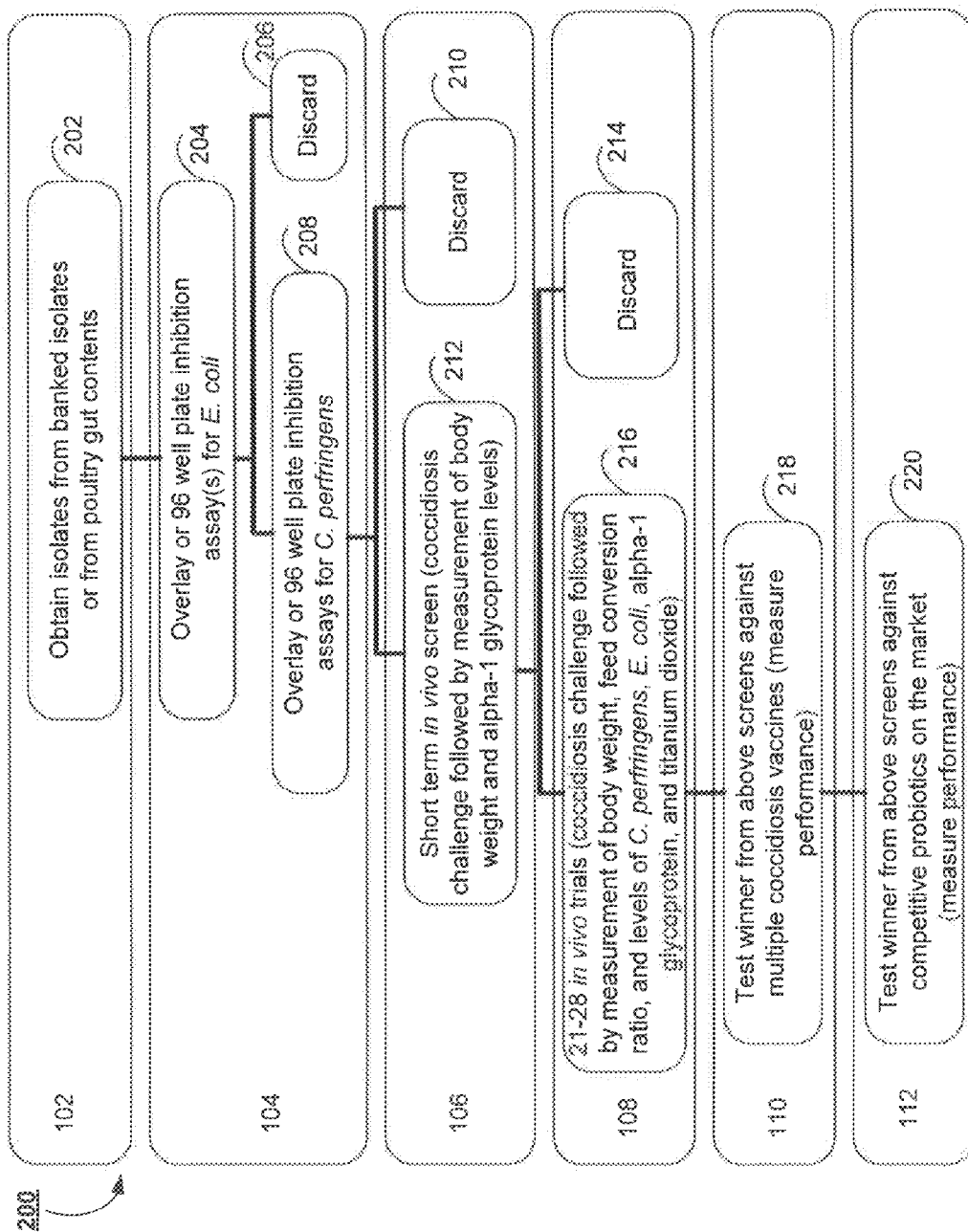
FIG. 2 further illustrates the selection process flow chart of FIG. 1, in accordance with various embodiments.

An example of a process to select bacteria which mitigates the negative reactions of the coccidiosis vaccine is illustrated in FIGS. 1 and 2. With reference to FIG. 1, method 100 is shown. Bacteria, for example, isolates, may be procured or otherwise obtained in (Step 102). For example, bacteria obtained in (Step 102) may be obtained from the GI tract of one or more poultry.

In vitro selection (Step 104) includes various steps to screen for certain properties of the bacteria outside a live animal vector. Isolates that perform satisfactorily will be advanced to future steps and may be referred to as screened isolates. In vivo selection (Step 106) may comprise the administration of one or more isolates to live vectors, such as chickens. The live vectors in (Step 106) may be measured for one or more bio-markers. Isolates that perform satisfactorily will be advanced to future steps and may be referred to as in vivo tested isolates. In multiple in vitro selection (Step 108), the live vectors may be measured for one or more bio-markers after administration of in vivo tested isolates. Isolates that perform satisfactorily will be advanced to future steps and may be referred to as multiple in vivo tested isolates. In conformational trial (Step 110), the multiple in vivo tested isolates are tested in vivo against a variety of coccidiosis vaccines. Isolates that perform satisfactorily will be advanced to future steps and may be referred to as confirmed isolates. In comparison trial (Step 112), the confirmed isolates are tested in vivo against a variety of coccidiosis vaccines. Isolates that perform satisfactorily will be advanced to future steps and may be referred to as confirmed isolates.

With reference to FIG. 2, in (Step 102), isolates are obtained commercially or from the GI tract of a poultry in (Step 202). Isolates may be grown in vitro, for example, in MRS medium at suitable temperatures for a suitable duration.

The resulting cultures may be plated on agar plates and overlaid with a medium containing one or more bacteria such as *E. Coli, Salmonella, C. perfringens*, etc. in (Step 204). After incubation, the cultures of bacterial samples that produce zones of inhibition in the overlays are selected for isolation. Bacterial samples that did not produce zones of inhibition are discarded. The selected colonies are then isolated on the same medium from which they are selected and incubated. In a second selection step (Step 208) the selected colonies are challenged against a population of another bacteria such as *C. perfringens*. After incubation, the new cultures of bacterial samples that produce zones of inhibition in the overlays are selected for further isolation. Those isolates with confirmed in vitro ability to inhibit growth in both (Step 204) and (Step 208) are amplified and selected for further analysis. Those isolates that did not are discarded in (Step 210).

Isolates which perform well in the in vitro testing are evaluated using a series of in vivo tests. The first in vivo test, (Step 106), is a short term screen. The bacterial isolates selected in the in vitro tests are given to a group of chicks on day-of-hatch along with a coccidiosis vaccine in (Step 212). A second group of chicks used as a control group are only given the coccidiosis vaccine. After a period of days, inflammatory bio-markers in the poultry are measured. Specifically, alpha-1 glycoprotein levels are measured in both control and treated poultry. Similarly, the body weight of the poultry is measured in both groups. Treated poultry that showed a significant increase in either weight or reductions in bio-markers when compared to the control group are noted. The bacteria those poultry are treated with will be selected for further evaluation. Poultry that showed little or no increase in weight or little to no reduction in inflammatory bio-markers are also noted. The bacteria that those poultry are treated with are then discarded in (Step 210).

Isolates which perform well in the in vivo testing in (Step 212) may be further evaluated using a multiple replicate in vivo trial in (Step 216). Similar to (Step 212), multiple groups of poultry are created. One is a control group only receiving the coccidiosis vaccine. The other groups receive both the coccidiosis vaccine and one or more bacterial isolates selected in previous in vivo tests. The vaccine and isolates are given to the poultry and chicks on day of age. Throughout the 14-28 days of the trial, the poultry receive tests relating to the various criteria. The test results are compared between the control group and the treated groups. The various criteria included body weight, feed conversion ratio, *C. perfringens* level, *E. coli* level, alpha-1 glycoprotein level and titanium dioxide level. Improvement of one or more of these criteria qualifies the isolate to advance. Measurements to obtain bacteria, alpha-1 glycoprotein, and titanium dioxide levels may be run at least twice during the trial. Body weight and or body weight gain measurements may be performed 3 times. A first measurement may be performed at day 5-7; a second measurement may be performed at around day 12-15; and a third measurement may be performed at around day 21-28 if the trial is continued to this point. Body weight may be the only measurement obtained at the final time point.

Isolates which performed well in the in vivo testing in (Step 216) are further evaluated by testing each isolate against several commercially available vaccines in Step (218). Those isolates that did not perform well are discarded in (Step 214). (Step 218) tests are similar to the tests in Step (216). Each isolate that performed as well or better than the results in Step 216 are selected as the final group of isolates.

The final group of isolates which perform well in other testing are further evaluated, in (Step 220), by comparing groups of poultry, where one group is given the coccidiosis vaccine and one of the selected isolates and the other group of poultry is given the coccidiosis vaccine and a commercial probiotic advertised to improve gut health.

In various embodiments, the bacteria are selected based on more than one criterion. A first group of bacteria may be selected by analysis of the specific bio-markers. A second group may be selected for reduction of a pathogen. A third group may be selected for improvement of production parameters. These selections may be done in parallel (i.e., selection of group 1, group 2 and group 3 at the same time from the original populations of bacteria). Also these selections may be done in order (i.e., selection of group 1 then selection of group 2 from samples in group 1 then selection of group 3 from samples in group 2). Also these sections may be done in parallel then subsequently screened against other criterion. In accordance with various embodiments, the selection criterion may be performed in any order. For example, the bio-markers may be used to form group 1, group 2, and/or group 3. Pathogen reduction may be used to form group 1, group 2, and/or group 3. Potentially the improvement of production parameters may be used to form group 1, group 2, and/or group 3. Any number of groups may be tested based on any criterion.

Figure 3:
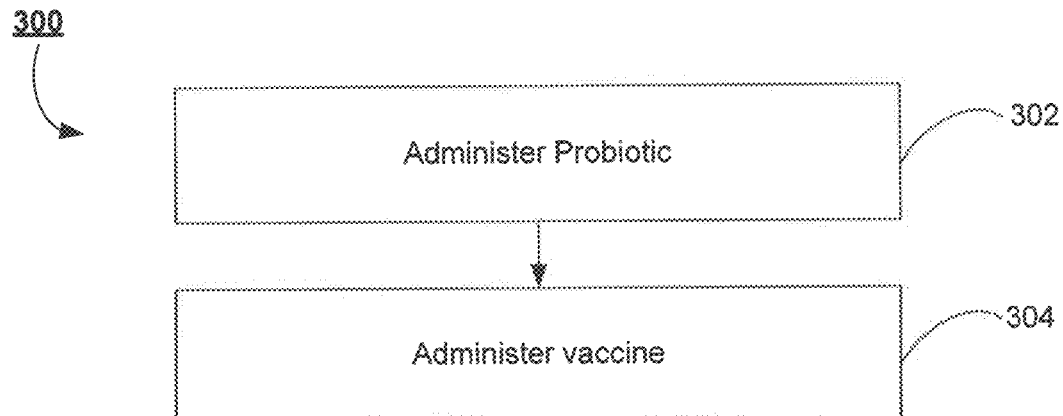
FIG. 3 illustrates an administration method according to various embodiments.

With reference to FIG. 3, administration method 300 is illustrated. A bacterium is administered in (Step 302). Administration may be via any suitable route, for example, the forms of administration discussed herein. The bacterium may comprise a confirmed isolate as determined by the process illustrated in FIG. 2. A coccidiosis vaccine is administered in (Step 304). Administration may be via any suitable route, for example, the forms of administration discussed herein.

Figure 4:
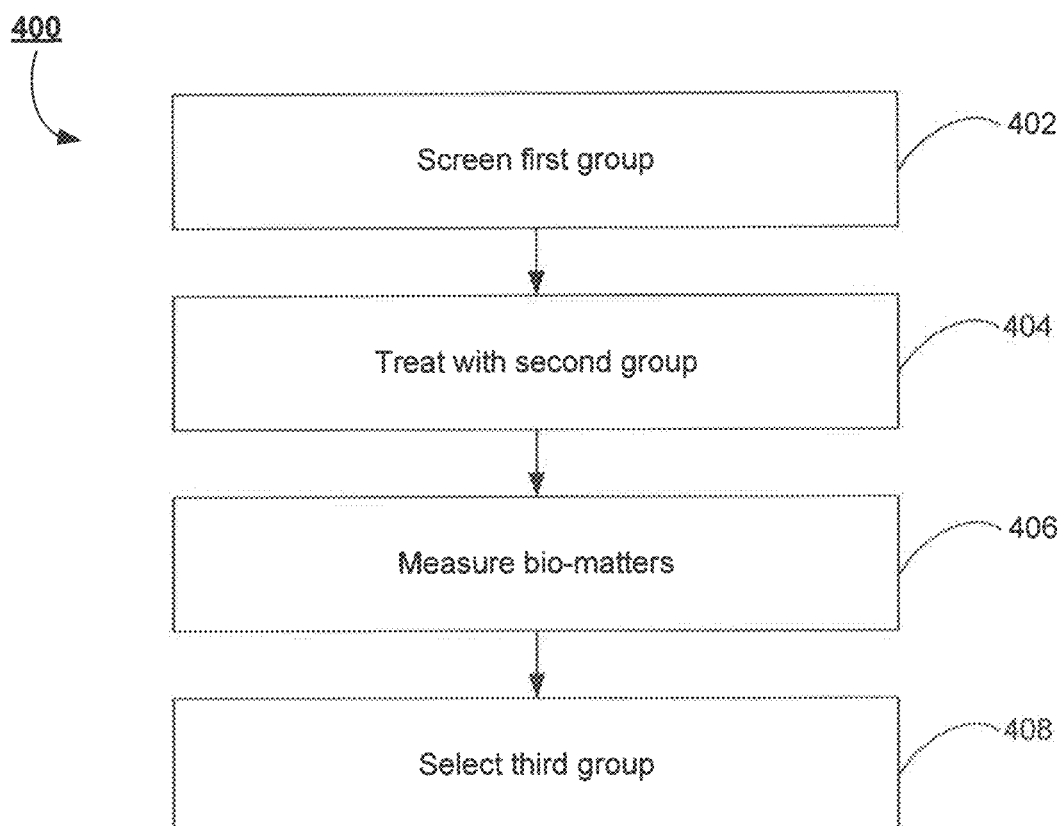
FIG. 4 illustrates a selection process, in accordance with various embodiments.

With reference to FIG. 4, selection method 300 is illustrated. A group of bacteria are screened for efficacy in inhibiting the growth of undesired bacteria in (Step 402). Screening may take place in vitro using any suitable method. (Step 402) yields an isolate that is administered to poultry in vivo in (Step 404). Administration may be via any suitable route, for example, the forms of administration discussed herein. The poultry are then tested for one or more bio-markers (Step 406). The presence of one or more criteria that are associated with positive outcomes in the in vivo study of (Step 406) are included in a final isolate in (Step 408).

Each bacterial selection is based on an evaluation of the bacteria that is most suitable to minimizing any adverse effects caused by the coccidiosis vaccine (i.e., criterion). These various selections produce a group of bacteria. Some isolated bacteria may be characterized by more than one criterion. While other isolated bacteria may be characterized by only a single criterion. Furthermore, some bacteria may be better at producing the criterion for which it is selected. An evaluation of the best bacteria for a single criterion or a combination of criteria is performed. The best performing bacteria is combined into a single probiotic for testing of the combined effect. The probiotic is further combined with a pharmaceutically acceptable excipient and/or carrier in a pharmaceutical composition. The pharmaceutical composition can include other additives included for the benefit of the poultry health. The additives may include a commercially available coccidiosis vaccine.

A bacterium is selected by determining those bacteria that reduce pathogens associated with secondary infections in poultry treated with a coccidiosis vaccine. Specifically, a bacterium may be selected by identifying those bacteria capable of reducing various pathogens which cause secondary GI infections in the GI tract of poultry during the period that the poultry is reacting adversely to the coccidiosis vaccine. The bacterium is selected in response to the bacterium inhibiting the growth, presence, and/or populations of bacteria that cause secondary infections associated with coccidiosis and/or the coccidiosis vaccine. Bacteria which inhibit the growth from the Enterobacteriaceae and Clostridiaceae families are selected. Specifically, the bacterial pathogen is selected from *Clostridium perfringens, Salmonella*, and/or *Escherichia coli*. The reduction of pathogens may vary depending on a variety of circumstances of the test. In one example, a bacterium may reduce the level of *C. perfringens, Salmonella*, and/or *E. coli* by at least one half log in the challenge model as compared to an untreated control.

The efficacy of the coccidiosis vaccine is assessed in relation to the bacteria selected. The assessment is to establish that the selected bacterium minimally or negligibly limits the efficacy of the coccidiosis vaccine. Any treatment including the selected bacterium is characterized such that after administration of both the treatment and the vaccine, the poultry still fully develops the immunity to coccidiosis as is typically caused by the vaccine. The treatment's effects on the efficacy of the coccidiosis vaccine are tested by measuring the number of oocytes excreted per gram of feces by the poultry. This may be accomplished by collecting feces for a set time period. The feces are then weighed and mixed into a saturated salt solution. The oocysts are collected from the solution, then counted using a McMasters counting chamber and microscope. Oocyst counting is a direct measurement of the reproduction of the *Eimeria* and is an indirect indicator or the health of the *Eimeria* replication.

Alternatively and/or additionally, the treatment's effects on the efficacy of the coccidiosis vaccine are tested by challenging a vaccinated bird treated with the selected bacterium with coccidiosis to verify the presence of immunity.

A bacterium is selected by determining those bacteria that provide an improved inflammatory response in the GI tract of poultry. Specifically, a bacterium may be selected by identifying those bacterium exhibiting decreasing or suppressive inflammation conditions in the GI tract of poultry. The selection may be undertaken by identifying certain bio-markers related to inflammation in the GI tract of poultry. Inflammatory bio-markers in the poultry are measured 5-7 days after treatment with a coccidiosis vaccine. More preferably, inflammatory bio-markers in the poultry are measured around 11-14 days after treatment with a coccidiosis vaccine. Specifically, alpha-1 glycoprotein levels are measured in both control and treated poultry. A decrease in the inflammatory bio-markers in the poultry having both the vaccine and the bacterium, as compared to poultry having only the vaccine, indicate that the bacterium should be selected as having the desirable anti-inflammatory characteristic. Furthermore, tests for gut barrier failure may also be used as an assessment of inflammation and gut health.

A bacterium is selected by determining that the bacterium that provides an improved food absorption response in the GI tract of poultry. Specifically, a bacterium may be selected by identifying those bacterium capable of decreasing the reduction of food absorption in the GI tract of poultry responding to a coccidiosis vaccine. Bacterium are selected which tend to increase the time a non-absorbable marker stays in the GI tract of poultry. Inflammatory bio-markers in the poultry are measured around 5-7 and around 11-15 days after treatment with a coccidiosis vaccine. Specifically, in this example, titanium dioxide is used as the indigestible marker. Titanium dioxide levels excreted from the poultry are measured in both control and treated poultry. The level of bio-marker excreted is measured over time. An increase in the time that the bio-marker spends in the poultry in response to the administration of a bacterium indicates that the bacterium should be selected as having the desirable increase in food absorption characteristic.

A bacterium is selected by determining the bacterium that provide improved intestinal morphology in the GI tract of poultry. Specifically, a bacterium may be selected by identifying those bacteria capable of healing the changes in the villus morphology in the GI tract of poultry caused by coccidiosis and/or a secondary infection associated with coccidiosis. The bacterium may be selected in response to the bacterium improving the villus height to crypt depth ration of probiotic treated poultry compared to a control group of poultry post coccidiosis vaccination. Similarly, the bacteria may be selected in response to the lamina propria thickness being decreased as compared to the control group.

A bacterium is selected by determining that the bacterium provides improved flock uniformity despite treatment of the flock with a coccidiosis vaccine. Specifically, a bacterium may be selected by identifying its capability of improving the flock uniformity post vaccination. The selection is in response to the bacterium improving the standard deviation of the body weight of probiotic treated poultry compared to a control group of poultry post vaccination with the coccidiosis vaccine.

A bacterium is selected by determining that the bacterium improves at least one or more production parameters in treated poultry compared to a control group. Specifically, a bacterium may be selected by identifying capability of improving one or more production parameters in the poultry. The production parameters include maintaining and/or increasing the poultry weight, maintaining and/or increasing feed conversion ratio, and/or decreasing morbidity or mortality of the poultry during infection due to the vaccine. Production parameters are assessed in chicks. The bacterium is selected in response to a demonstration of the improvement of one or more production parameters. The bacterium allows the poultry to continue to develop, during the period of the adverse effect due to the coccidiosis vaccine, at a rate improved over that of vaccinated poultry not treated with the bacterium.

A bacterium is selected by determining that the bacterium improves the body weight of the poultry treated with the bacterium and a coccidiosis vaccine when compared to a control group of poultry. Specifically, a bacterium may be selected by identifying a bacterium capable of improving the body weight of poultry receiving a coccidiosis vaccine. The bacterium is selected and combined into a treatment in order to increase the weight gain of the treated poultry compared to the weight gain of untreated poultry. Bacterium which increases body weight on the poultry during the period of the adverse effect due to the vaccine is selected. Similarly, bacterium that increases the body weight of the poultry at any point during the poultry's life can be selected. This measurement is taken in the adverse effect period, after the adverse effect period and/or continually during the life of the bird or population.

A bacterium is selected by determining that the bacterium provides an improved food conversion ratio absorption response in the GI tract of poultry. Specifically, a bacterium may be selected by identifying a bacterium capable of improving the poultry's feed conversion ratio. The bacterium is selected and combined into a treatment in order to improve the feed conversion ratio during the 1-4 week period post-vaccination. Bacterium which increases feed conversion ratio during the period the poultry is reacting to the vaccine is selected. Similarly, bacterium that increases the feed conversion ratio at any point during the poultry's life may be selected. Feed conversion is measured by creating a ratio of the food that each bird or bird population consumes with the increase in the body weight of the bird or the body weight of the bird population. The feed conversion ratio is calculated for a given period using the following formula: (total body weight gain)/(total feed consumed). The treated birds and control birds ratios are then compared to determine the efficacy of the bacteria and/or treatment. This measurement is taken in the reactive period, after the reactive period and/or continually during the life of the bird or population.

Various coccidiosis vaccines are administered to poultry via different routes and at different times. As such, treatment with the bacterium may vary depending on the coccidiosis vaccine being used. For example, Inovocox vaccines are delivered in ovo. A bacterium may be characterized by improving one or more criteria when administered after hatch of poultry that received a vaccination in ovo. For instance the vaccine may be administered in ovo and the probiotic may be administered to newly hatched chickens via spray, feed, or water administration.

While not bound by theory, it is believed that the treatments (and any bacterium comprising such treatments) discussed herein modulate innate and/or adaptive immune response systems. For example, the selected bacterium and treatment may directly reduce inflammation conditions caused by the innate immune response. The reduction of inflammation in the GI tract then reduces GI-related stress and other inflammatory related stresses and conditions in the poultry while the poultry's adaptive immune response develops. In another example, treatments in accordance with the invention may also reduce certain secondary bacterial infections, thereby preventing such further infections and further inflammatory conditions from developing. Thus, by isolating bacteria as discussed herein, the isolates are specifically suited to the specific purpose modulating the innate immune response, and potentially adaptive immunity, of the poultry, and thus improving the overall health of the poultry.

EXAMPLE 1

The ability of probiotic formulations to minimize the reduction of average daily weight gain in broiler chicks following the use of anticoccidial vaccines through the concomitant treatment with a lactic acid bacteria-based probiotic was investigated. Experiments were performed to develop a probiotic formulation comprising poultry specific lactic acid bacteria for administration to neonatal broiler chicks (day-of-hatch) to reduce the early performance reductions observed after vaccination with *Eimeria* vaccines. The formulations were prepared for mass administration in hatcheries to neonatal chicks vaccinated against *Eimeria*. Bacterial isolates having the ability to colonize all areas of the neonatal gastrointestinal tract and improve early growth rate of the chicks were selected. The formulations capable of out competing other bacteria within the gastrointestinal tract were selected.
Strain Selection Samples were extracted from the gut of chickens by opening up the desired part of the gastrointestinal (GI) tract then removing digesta and/or scraping the mucosa. Bacterial samples were extracted from the gut contents of the chickens by macerating the duodenum, ileum and ceca from young chickens. The samples, kept separate for each area of the gastrointestinal tract, were then added to MRS (de Man, Rogosa, Sharpe) medium (Sigma-Aldrich, St. Louis, Mo.) and incubated aerobically and anaerobically at 37° C.-42° C. for 12 hours-24 hours. Cultures were passaged twice. The resulting cultures were plated on MRS agar plates, then overlaid with a soft agar containing a population of $10^6$ to $10^8$ cfu *E. coli* isolated from commercial poultry. After incubation, the cultures of bacterial samples that produced zones of inhibition in the overlays were selected as individual colonies for isolation. Bacterial samples that did not produce zones of inhibition were discarded. The selected colonies were then isolated on the same medium from which they were selected and incubated. Isolates were grown together to identify bacteria that can grow together. Combinations of surviving isolates were tested to determine the best options.

In a second selection step the selected colonies were challenged against a population of $10^6$ to $10^8$ cfu of *C. perfringens* isolated from commercial poultry. After incubation, the new cultures of bacterial samples that produce zones of inhibition against *C. perfringens* in the overlays were selected for further isolation. Those isolates with confirmed in vitro ability to inhibit *E. coli* and *C. perfringens* growth were amplified and selected for further analysis as probiotic candidates (PC1, PC2, PC3, PC4 and PC5).

Experiment 1

Figure 5A:
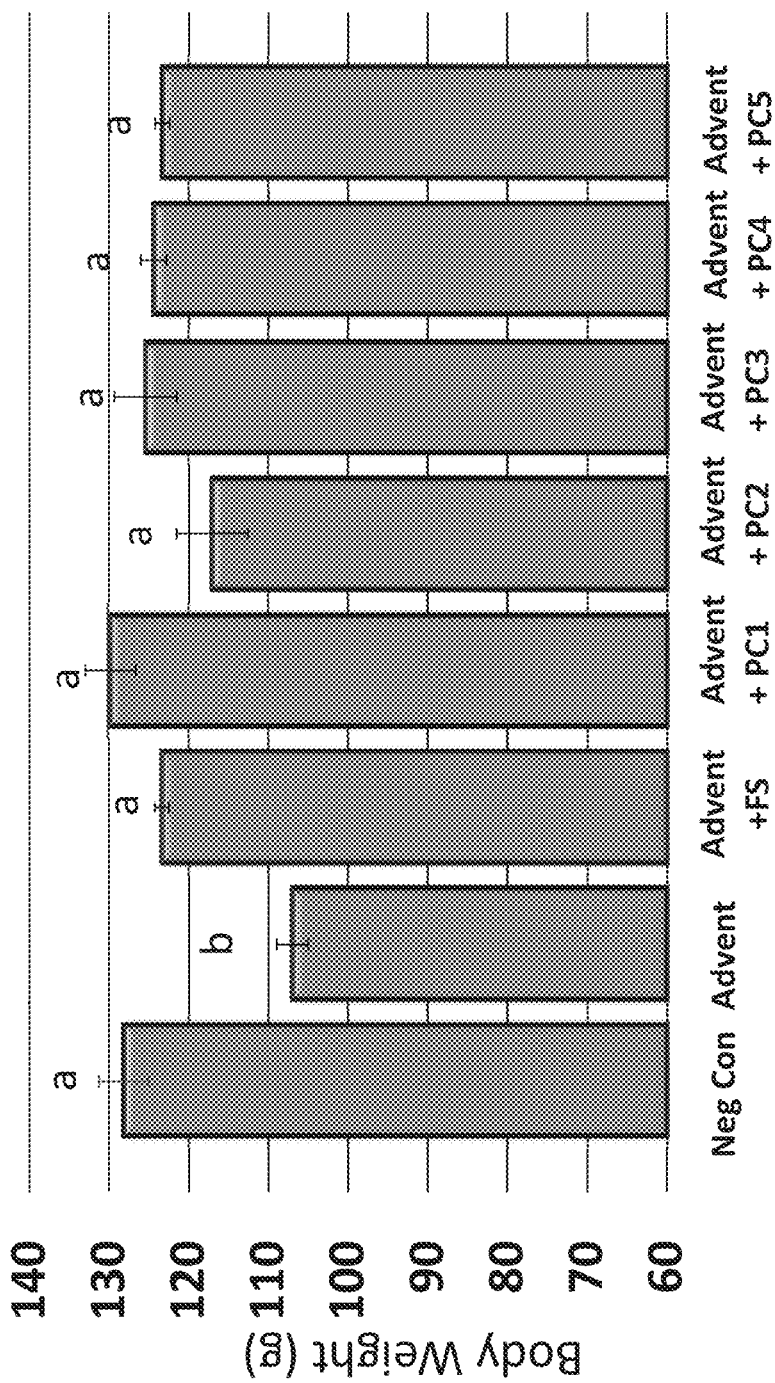
FIG. 5A illustrates body weight at day 7.
Figure 5B:
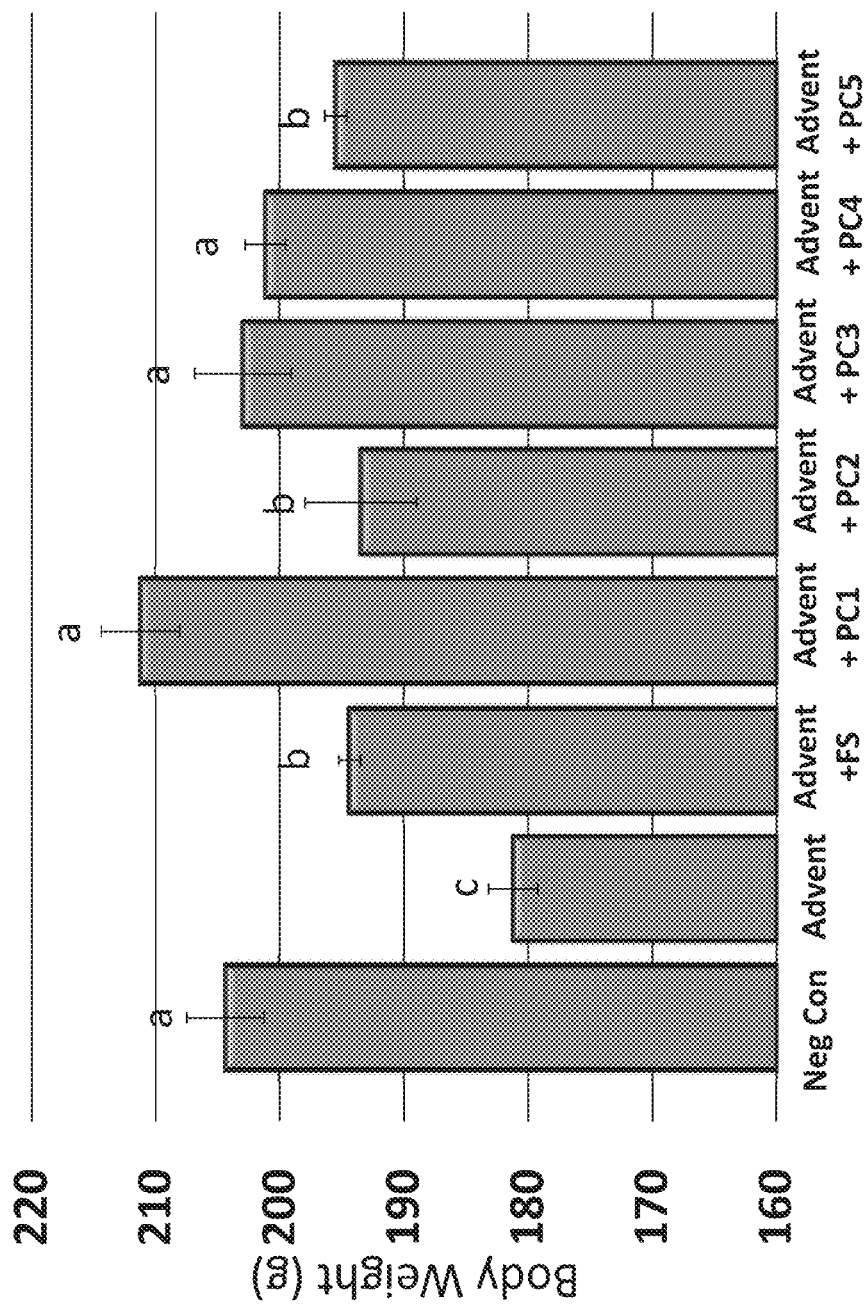
FIG. 5B illustrates body weight at day 10.
Figure 5C:
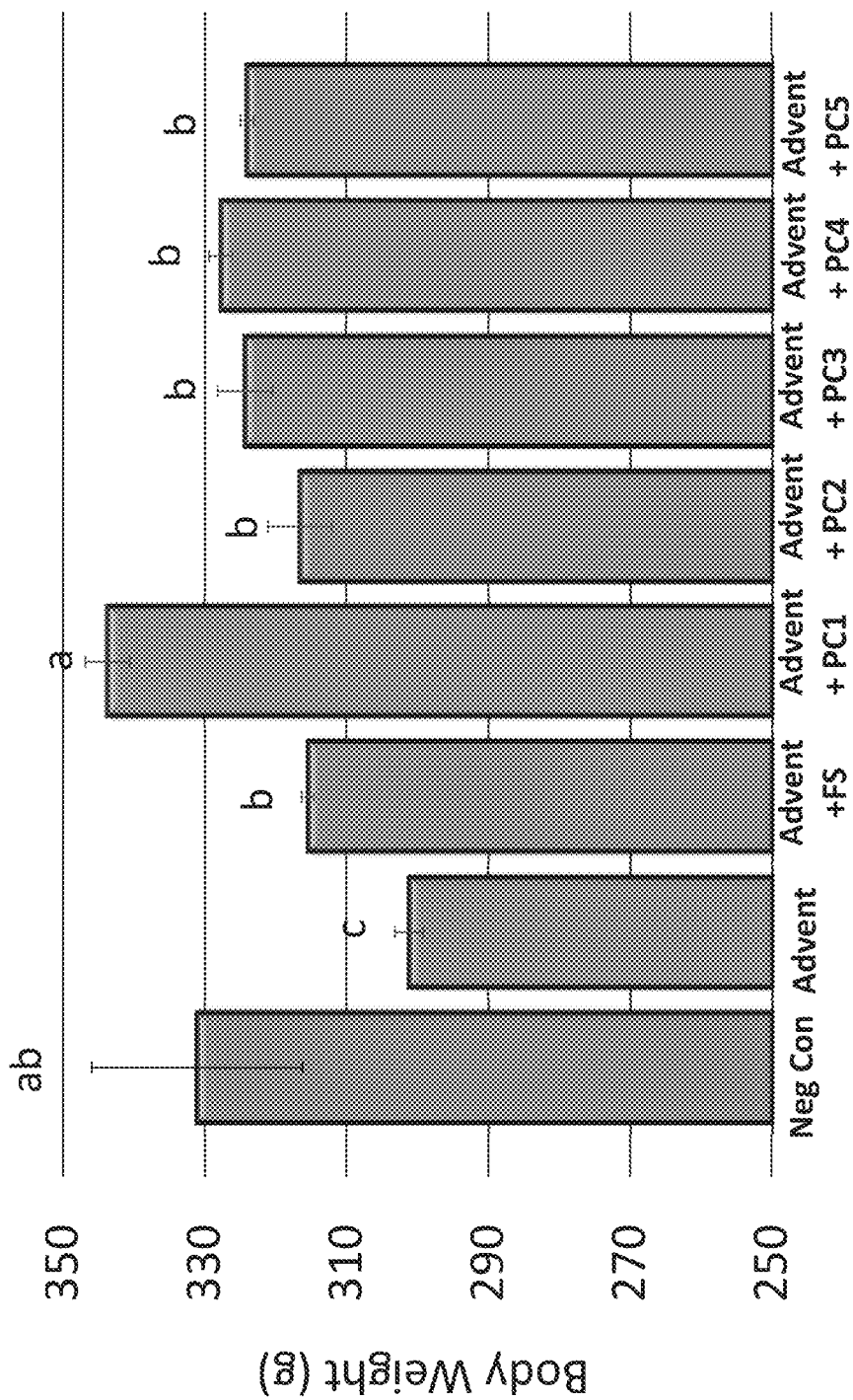
FIG. 5C illustrates body weight at day 14. Columns denoted by different letters are significantly different; "a" is significantly different than "b" and "c", and "b" is significantly different from "c" ($p<0.05$).

Experiment 1 was performed to determine if any of the probiotic candidates could reduce or eliminate the reduction on body weight gain associated coccidiosis vaccination. The negative control (Neg Con) was administered saline. This group was used as a baseline for normal broiler chick performance. The vaccine only group (Advent) received a label dose of a coccidiosis vaccine. The difference between these two groups represents the loss in production of a vaccinated flock. A commercial probiotic designed for neonatal broiler chicks was administered concurrently with the vaccine (Advent+FS). This group serves as a minimum performance baseline with which to compare probiotic candidates. The probiotic candidates (PC1, PC2, PC3, PC4, PC5) were combinations of isolates which performed well in the in vitro testing and were evaluated using a series of in vivo tests. Briefly, day-of-hatch chicks were randomized and placed into groups (5 reps per group, n=20/rep). The bacterial isolates selected in the in vitro tests (probiotic candidate 1 (PC1), probiotic candidate 2 (PC2), probiotic candidate 3 (PC3), probiotic candidate 4 (PC4), and probiotic candidate 5 (PC5)) were given to a group of neonatal chicks on day-of-hatch along with a commercial coccidiosis vaccine (ADVENT® coccidiosis vaccine, Huvepharma, Inc., Peachtree City, GA). Sterile saline was given as a negative control to one group of chicks (Neg Con). A second group of chicks used as a control group were only given the ADVENT® coccidiosis vaccine (Advent). One group of chicks was given the ADVENT® coccidiosis vaccine and a FLORASTART® probiotic (Pacific Vet Group-USA, Fayetteville, AR) (Advent +FS) as a positive control. Chicks were given 1 x $10^6$ cfu of a probiotic candidate cocktail or sterile saline by oral gavage. All chicks were given free access to feed and water and kept at age appropriate temperatures for the duration of the trial. The body weight of the poultry was measured in both groups at days 7 (FIG. 5A), 10 (FIG. 5B) and 14 (FIG. 5C) ("a" is significantly different than "b" and "c", and "b" is significantly different from "c", p<0.05). All probiotic treated poultry showed a significant increase in weight when compared to the Advent. Surprisingly, one group, PC1, performed equally as well as the Neg Con group at all time points measured. The PC1 group was numerically superior but statistically similar at days 7, 10, and 14 in terms of body weight. Probiotic candidate 1 (PC1) was selected for further testing due to these promising results. It was noted that neither the commercial probiotic (FS) nor the other probiotic candidate combinations demonstrated the ability to match the body weight of the Neg Con group through the measured period. Initial cycling of the oocysts leads to damage to the intestinal tract of vaccinated birds at 5-6 days post vaccination. At day 7 the vaccine only group (Advent), had a significantly lower body weight than all other groups (FIG. 5A). There was no significant difference noted between any of the other groups. At day 10, the body weight of the Neg Con and PC1 groups was significantly higher than the vaccine only group (FIG. 5B), At day 14 the body weight of the chicks was varied among the probiotic candidates but no significant difference was observed between the probiotic candidates and the Neg Con (FIG. 5C). However, the chicks administered PC1 showed an increase in body weight compared to the Neg Con group. Birds treated with PC1 following vaccination with an *Eimeria* vaccine, appeared to perform better than birds that were not vaccinated and birds that did not receive an intestinal challenge (Neg Con).

Experiment 2

Isolates which performed well in the in vivo testing in Experiment 1 were further evaluated using a multiple replicate in vivo trial. Probiotic candidate 1 (PC1) was selected for further testing. This probiotic candidate comprised a cocktail of lactic acid bacteria identified by biochemical and 16s RNA analysis (*Lactobacillus salivarius* PVG-886, *Pediococcus pentosaceus* PVG-1180 and *Lactobacillus salivarius* PVG-869) was selected and subjected to further testing. These bacterial isolates were deposited with the Agricultural Research Service Culture Collection (NRRL), 1815 North University Street, Peoria, Ill. 61604, U.S.A. and assigned accession numbers NRRL B-67032 (*Lactobacillus salivarius*, PVG-886), NRRL B-67030 (*Pediococcus pentosaceus*, PVG-1180) and NRRL B-67031 (*Lactobacillus salivarius*, PVG-869). The bacterial isolates were mailed by Federal Express to the NRRL by Ross Wolfenden of Pacific Vet Group —USA, Inc. on Mar. 26, 2015.

Figure 6:
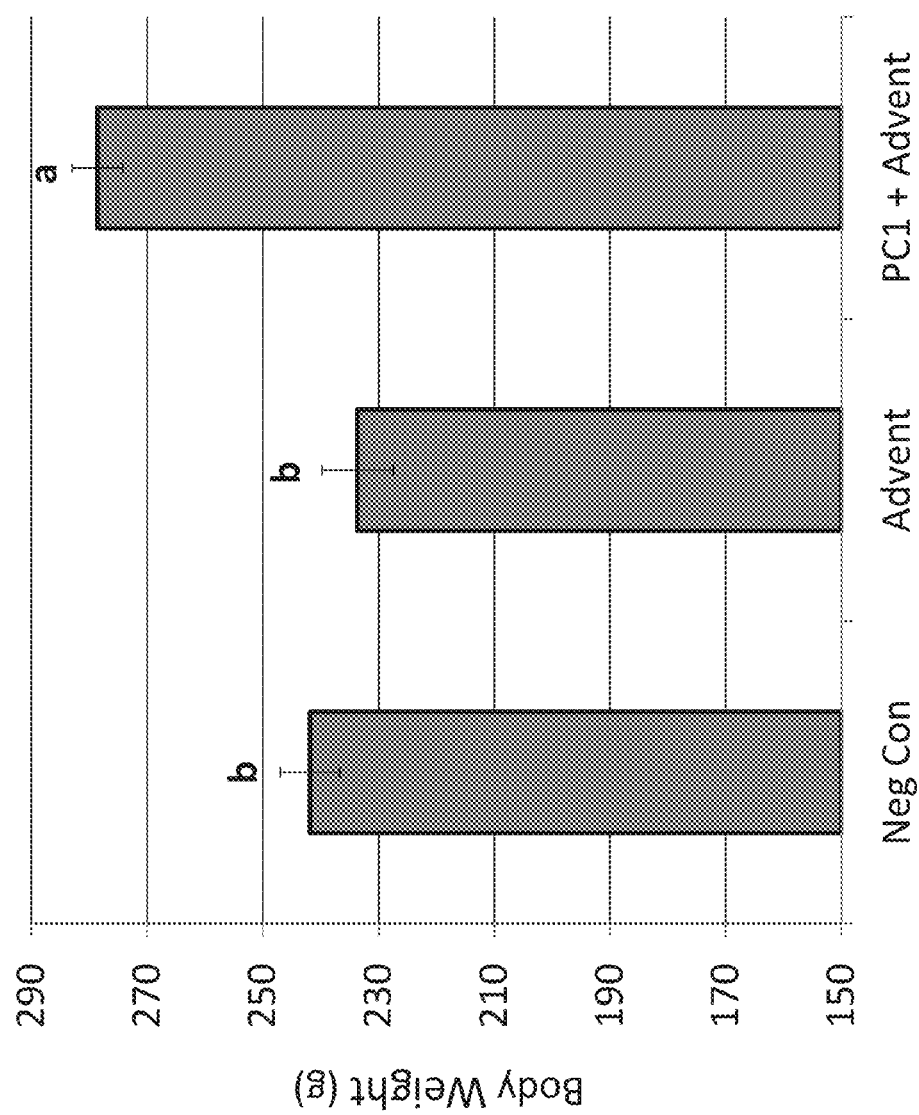
FIG. 6 illustrates body weight measurement of chicks at day 10 in Experiment 2. Saline negative control (Neg Con), ADVENT® coccidiosis vaccine (Advent), ADVENT® coccidiosis vaccine and probiotic candidate 1 (Advent+PC1). Columns denoted by different letters are significantly different; "a" is significantly different than "b" ($p<0.05$).

Poultry were placed into multiple groupings for the study. Day-of-hatch chicks were randomized and placed into groups (7 reps per group, n=20/rep). The objective was to test the ability of PC1 to reduce the difference between the control group (Neg Con) as compared to the groups that received only a commercial vaccine (Advent, HatchPakIII, and CocciVacB) without PC1. A first control group received only the ADVENT® coccidiosis vaccine control (Advent). A second control group received sterile saline as a negative control (Neg Con). The other groups received both the ADVENT® coccidiosis vaccine and the bacterial isolate probiotic candidate 1 (Advent +PC1) selected in the previous in vivo tests. The vaccine and PC1 were given to the poultry and chicks on day of age. Chicks were given $1 \times 10^6$ cfu of probiotic candidate 1 or sterile saline by oral gavage. All chicks were given free access to feed and water and kept at age appropriate temperatures for the duration of the trial. Throughout the 14 days of the trial, the poultry received tests relating to the various criteria. The test results were compared between the control group and the treated groups. The various criteria included body weight and/or villus development within the gastrointestinal tract ratio. Improvement of one or more of these criteria qualified the isolate(s) to advance. Body weight and or body weight gain measurements were performed 3 times. A first measurement was performed at around day 5-7; a second measurement was performed at around day 9-10; and a third measurement was performed at around day 12-15. The chicks were weighed at day 7, 10 and 14 (FIG. 6, body weight at day 10; "a" is significantly different than "b", $p<0.05$ ). Body weight may be the only measurement obtained at the final time point. The PC1 treated group, even though challenged by vaccination, performed significantly better than the vaccine only group (Advent) and in this case the control (Neg Con) as well. These results, surprisingly, indicate that vaccinated birds which also receive PC1 perform above the level of unvaccinated birds.

Experiment 3

Figure 7:
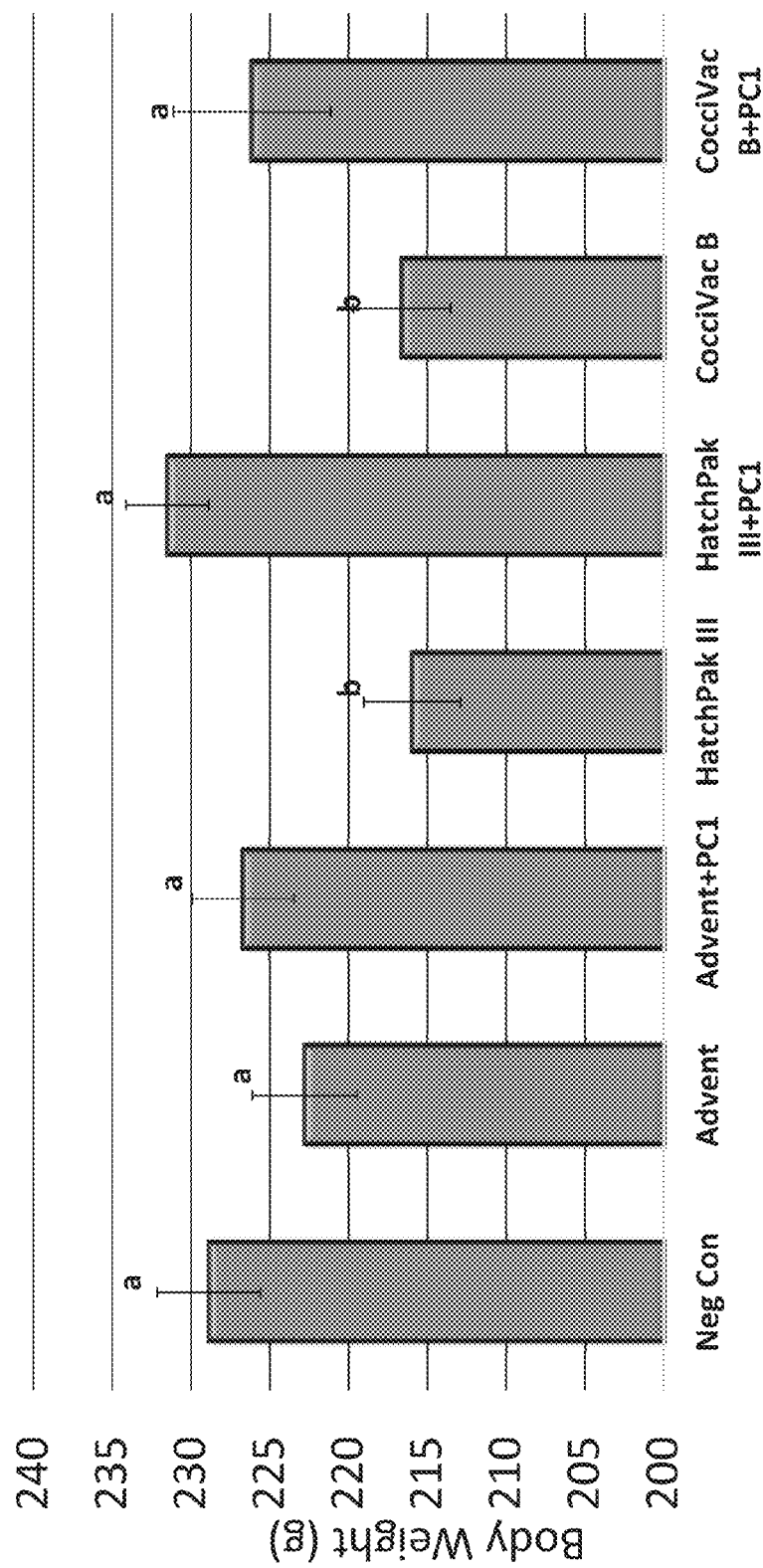
FIG. 7 illustrates body weight measurement of chicks with and without probiotic in Experiment 3. Saline control (Neg Con), ADVENT® coccidiosis vaccine (Advent), ADVENT® coccidiosis vaccine and probiotic candidate 1 (Advent +PC1), HATCHPAK®COCCI III coccidiosis vaccine (HatchPak III), HATCHPAK®COCCI III coccidiosis vaccine and probiotic candidate 1 (HatchPak III +PC1), COCCIVAC®-B oocyst coccidiosis vaccine (CocciVac B), COCCIVAC®-B oocyst coccidiosis vaccine and probiotic candidate 1 (CocciVac B +PC1). Columns denoted by different letters are significantly different; "a" is significantly different than "b" ($p<0.05$).
Figure 8:
FIG. 8 illustrates a cross section of an ileum from 7 day old vaccinated chicks in Experiment 4.
Figure 8:
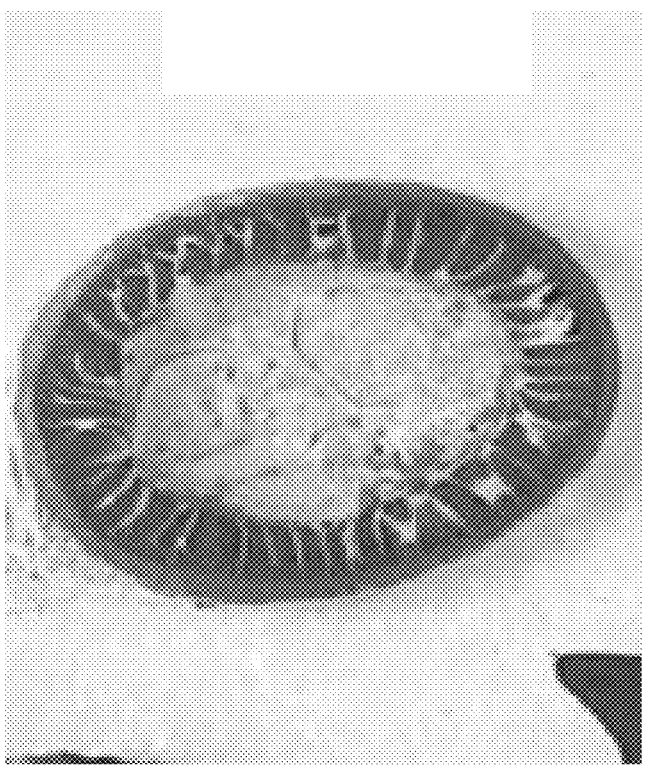
Figure 9:
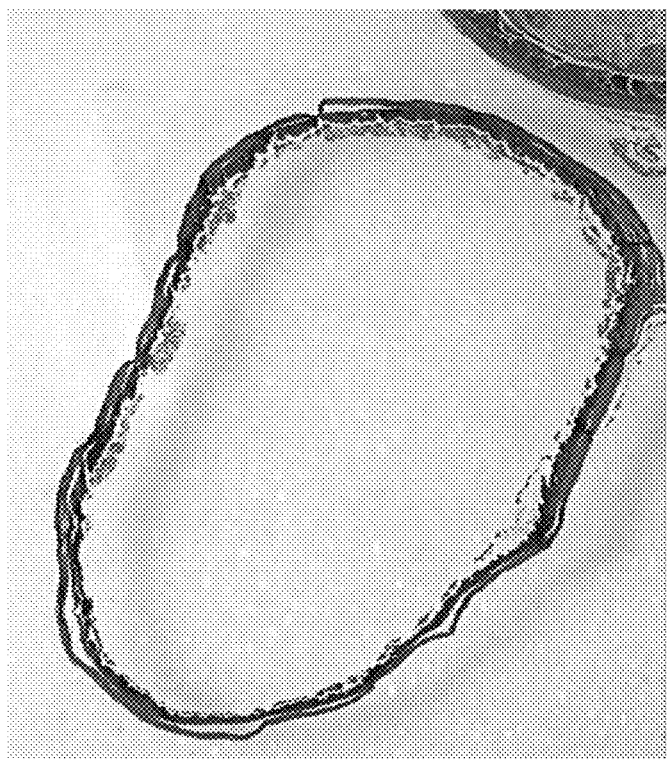
FIG. 9 illustrates a cross section of a ceca from 7 day old vaccinated chicks in Experiment 3.
Figure 9:
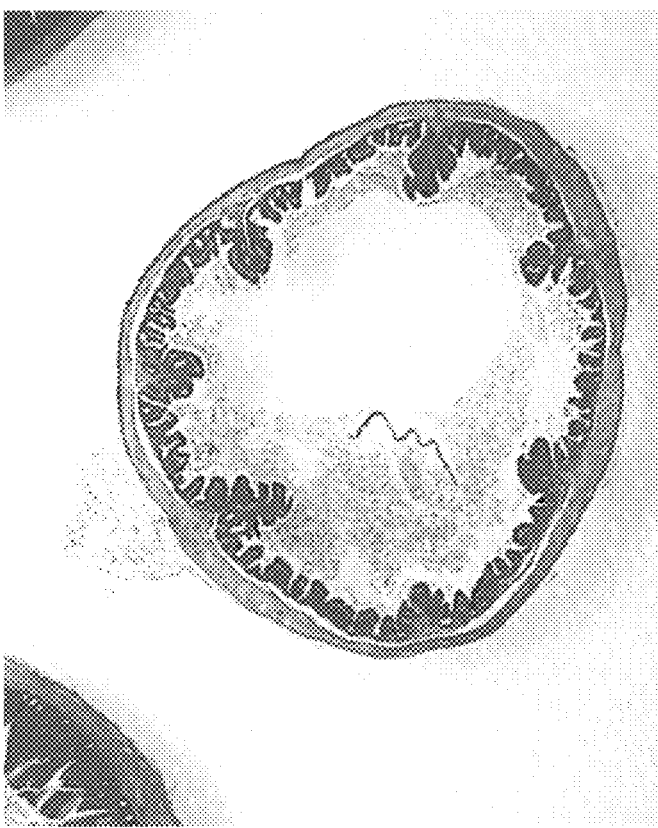
Figure 10:
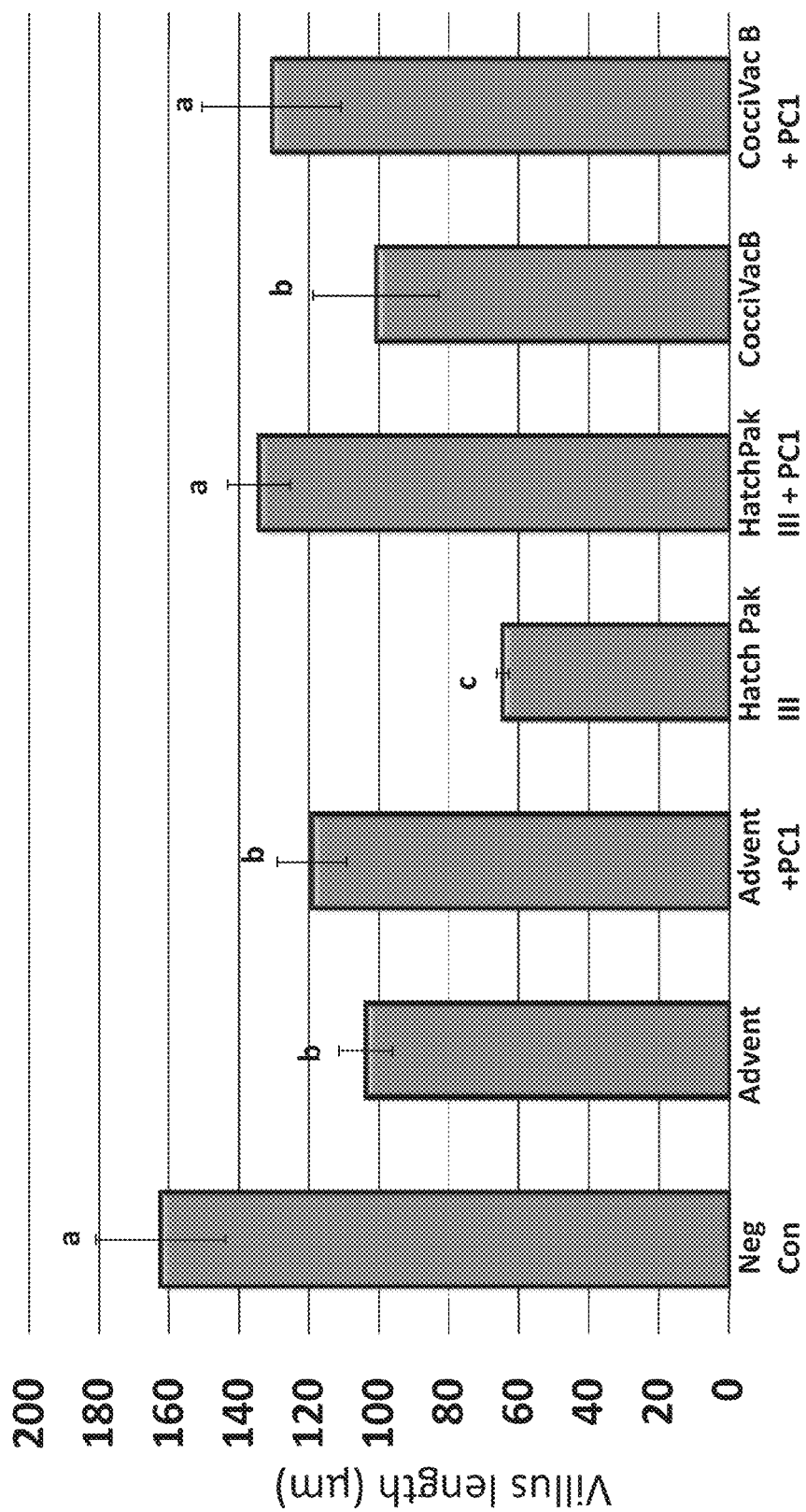
FIG. 10 illustrates the effects of a probiotic on villus length of the ileum in Experiment 3. Saline control (Neg Con), ADVENT® coccidiosis vaccine (Advent), ADVENT® coccidiosis vaccine and probiotic candidate 1 ( Advent +PC1), HATCHPAK®COCCI III coccidiosis vaccine (HatchPak III), HATCHPAK®COCCI III coccidiosis vaccine and probiotic candidate 1 (HatchPak III +PC1), COCCIVAC®-B oocyst coccidiosis vaccine (CocciVac B), COCCIVAC®-B oocyst coccidiosis vaccine and probiotic candidate 1 (CocciVac B +PC1 ). Columns denoted by different letters are significantly different; "a" is significantly different than "b" and "c", and "b" is significantly different from "c" ($p<0.05$).

Isolates which performed well in the multiple replicate in vivo testing of Experiment 2 were further evaluated by testing each isolate against several commercially available vaccines. As above, the objective was to test the ability of PC1 to reduce the difference between the control group (Neg Con) as compared to the groups that received only a commercial vaccine (Advent, HatchPakIII, and CocciVacB) without PC1. Tests were similar to those described above. Day-of-hatch chicks were randomized and placed into groups (5 reps per group, n=20/rep). Chicks were vaccinated with one of three commercial *Eimeria* vaccines, ADVENT® coccidiosis vaccine; HATCHPAK®COCCI III coccidiosis vaccine (Merial, Duluth, Ga.); COCCIVAC®-B oocyst coccidiosis vaccine (Merck, Madison, NJ) or a dose of sterile saline as a negative control. The seven groups were as follows: Saline control (Neg Con), ADVENT® coccidiosis vaccine (Advent), ADVENT® coccidiosis vaccine and probiotic candidate 1 (Advent +PC1), HATCHPAK®COCCI III coccidiosis vaccine (HatchPak III), HATCHPAK®COCCI III coccidiosis vaccine and probiotic candidate 1 (HatchPak III +PC1), COCCIVAC®-B oocyst coccidiosis vaccine (CocciVac B), and COCCIVACO® -B oocyst coccidiosis vaccine and probiotic candidate 1 (CocciVac B +pC1 ). Chicks were given 1 $\times 10^6$ cfu of the probiotic candidate 1 or sterile saline by oral gavage. All chicks were given free access to feed and water and kept at age appropriate temperatures for the duration of the trial. The chicks were weighed at day 7, 10 and 14 (FIG. 7, body weight at day 10 of vaccinated chicks with and without probiotic; "a" is significantly different than "b", $p<0.05$). On day 7, ileum (FIG. 8A, ADVENT® coccidiosis vaccine +probiotic candidate 1, FIG. 8B, ADVENT® coccidiosis vaccine) and ceca (FIG. 9A, ADVENT® coccidiosis vaccine +probiotic candidate 1, FIG. 9B, ADVENT® coccidiosis vaccine) were collected from the chicks and the tissues were sectioned and stained. The villi lengths were measured and the vaccine only and vaccine plus probiotic lengths were compared (FIG. 10, ADVENT® coccidiosis vaccine, HATCHPAK®COCCI III coccidiosis vaccine, COCCIVAC®-B oocyst coccidiosis vaccine; "a" is significantly different than "b" and "c", and "b" is significantly different from "c", $p<0.05$). The birds treated with PC1 had numerically higher body weights and villus lengths as compared to the vaccine only groups. In the case of groups vaccinated with HatchPakIII or CoccivBacB, treatment with PC1 significantly improved these parameters. None of the PC1 treated groups weighed less than the Neg Con group, indicating that despite intestinal insult by the various vaccines, PC1 helped maintain optimal performance. This indicates that the severity of the impact by the vaccines was reduced for all PC1 treated groups.

Experiment 4

Figure 11A:
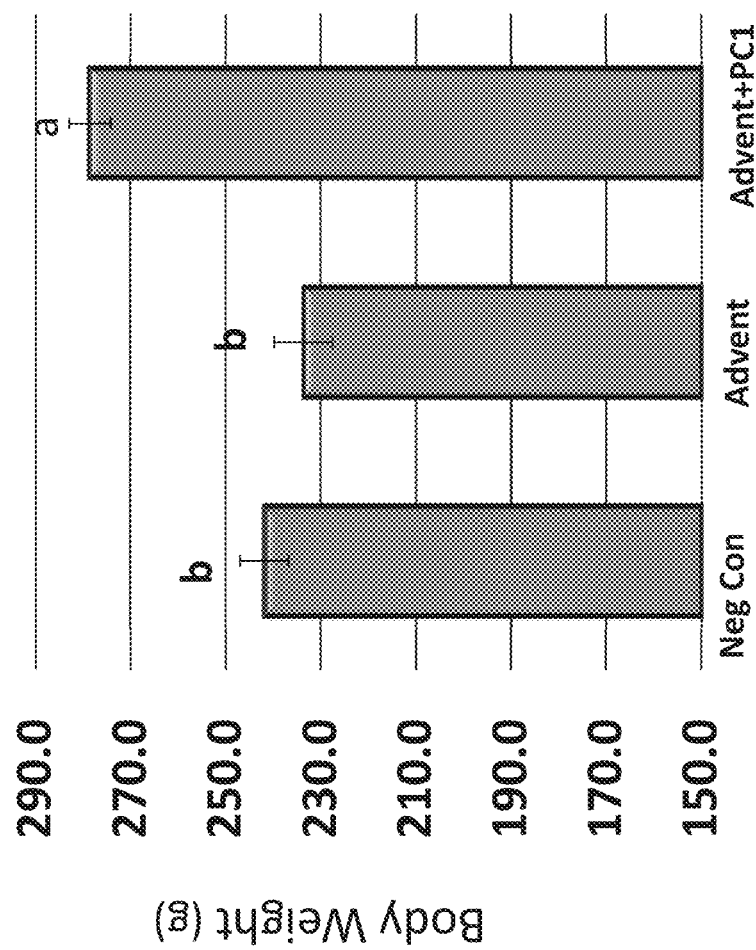
FIG. 11A illustrates body weight measurements at day 10.
Figure 11B:
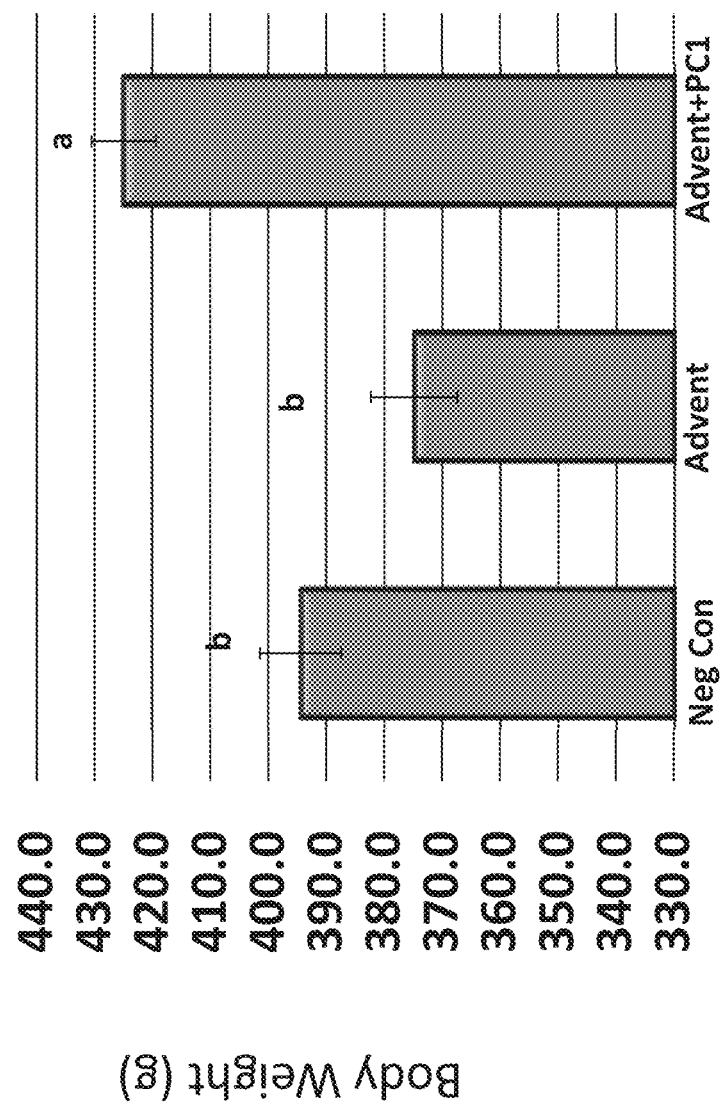
FIG. 11B illustrates body weight measurements at day 14. Columns denoted by different letters are significantly different; "a" is significantly different than "b" ($p<0.05$).
Figure 12:
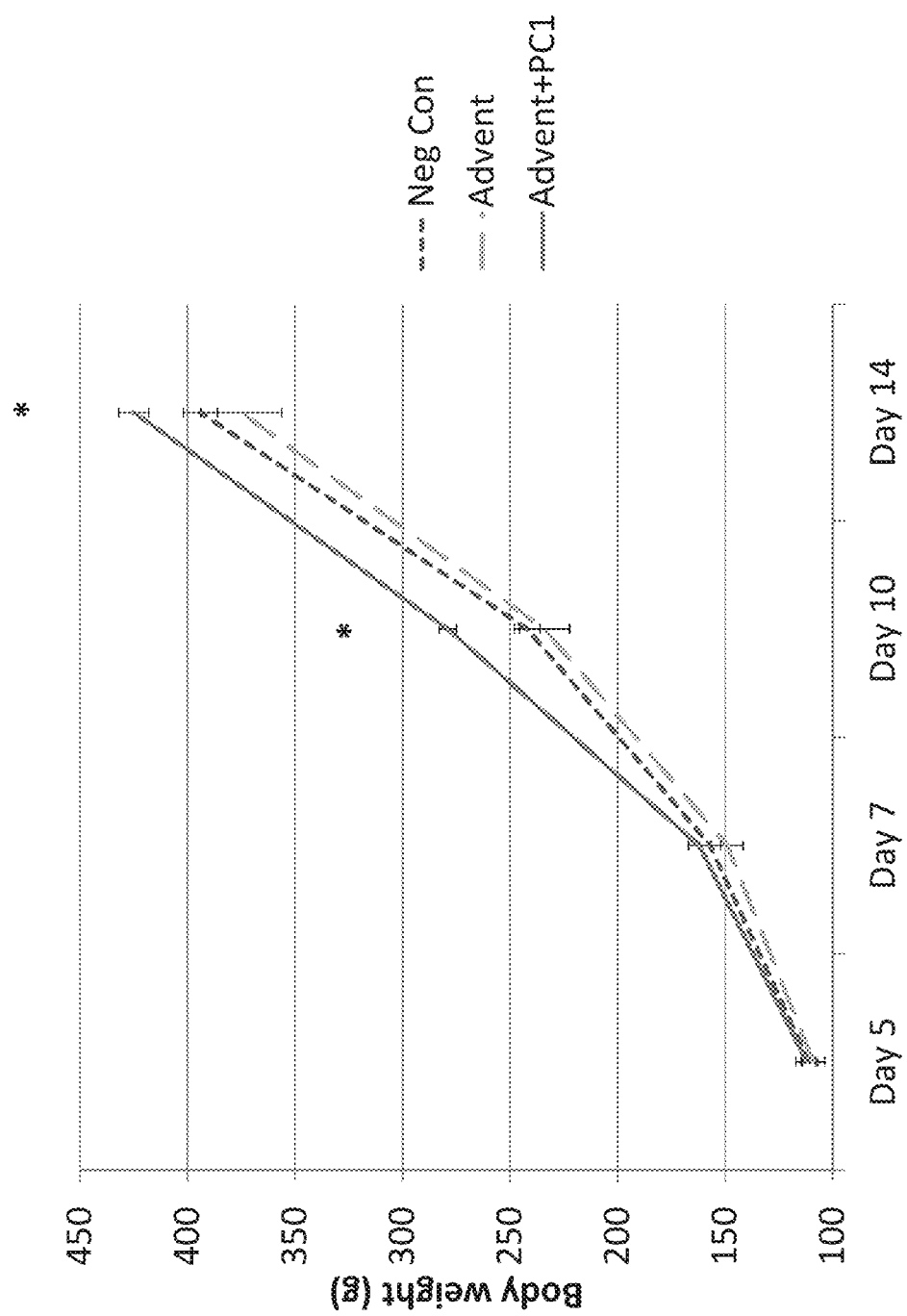
FIG. 12 illustrates body weight trends at day 5, 7, 10 and 14, in Experiment 4. Saline control (Neg Con), ADVENT® coccidiosis vaccine (Advent), and ADVENT® coccidiosis vaccine and probiotic candidate 1 (Advent+PC1), A "*" denotes a significant difference between Advent +PC1 and Neg Con and Advent, $p<0.05$,.
Figure 13:
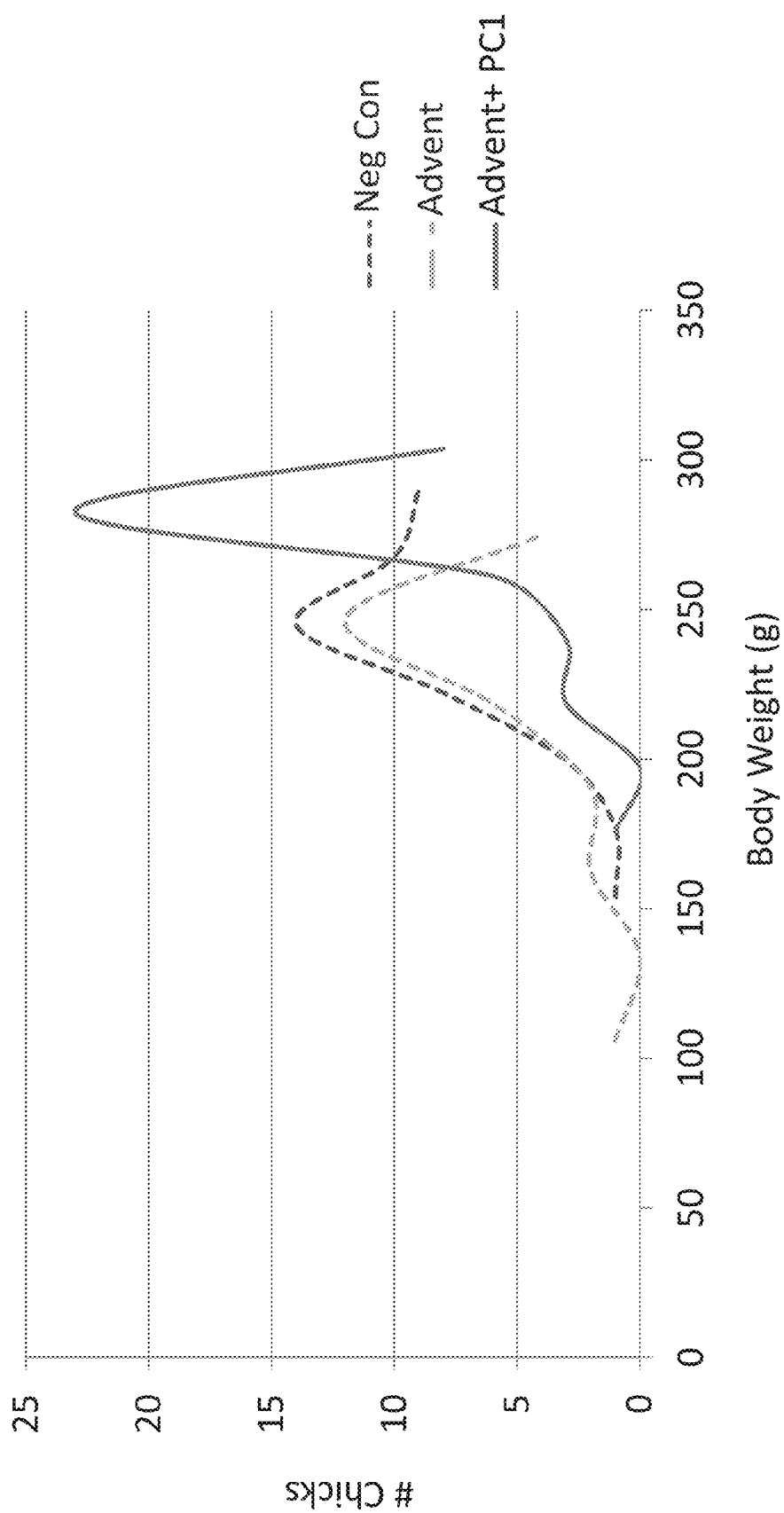
FIG. 13 illustrates weight distributions of chicks at day 10. Saline control (Neg Con), ADVENT® coccidiosis vaccine (Advent/dotted line), ADVENT® coccidiosis vaccine and probiotic candidate 1 (Advent +PC1 ).

The final group of isolates which performed well in Experiment 2 and 3 (PC1) testing were further evaluated, by comparing groups of poultry, where one group was given the ADVENT® coccidiosis vaccine and one of the selected isolates and the other group of poultry was given the ADVENT® coccidiosis vaccine and probiotic candidate 1 (PC1). The objective was to limit any reduction in performance associated with vaccination. Day-of-hatch chicks were randomized and placed into groups (7 reps per group, n=20/rep). Chicks were vaccinated with a commercial *Eimeria* vaccine, ADVENT® coccidiosis vaccine (Advent), or a dose of sterile saline (Neg Con) as a control. Chicks were given $1 \times 10^6$ cfu of the probiotic candidate 1 or sterile saline by oral gavage. All chicks were given free access to feed and water and kept at age appropriate temperatures for the duration of the trial. Chicks were weighed at day 5, 7, 10 and 14. A 16.2% increase in body weight on day 10 (FIG. 11A, "a" is significantly different than "b", $p<0.05$) and an 11.8% body weight increase on day 14 (FIG. 11B, "a" is significantly different than "b", $p<0.05$) was observed. FIG. 12 illustrates the increase in body weight from day 5, 7, 10 and 14 (saline (Neg Con), ADVENT® coccidiosis vaccine (Advent), and ADVENT® coccidiosis vaccine and probiotic candidate 1 (Advent +PC1); A "*" denotes a significant difference between Advent +PC1 and Neg Con and Advent, $p<0.05$. Weight distributions of the chicks at day 10 were compared (FIG. 13, control/saline (Neg Con), ADVENT® coccidiosis vaccine (Advent), ADVENT® coccidiosis vaccine and probiotic candidate 1 (Advent +PC1)). The PC1 treated group, even though challenged by vaccination, performed significantly better than the vaccine only group (Advent) and in this case the control (Neg Con) as well. These results, surprisingly, indicate that vaccinated birds which also receive PC1 perform above the level of unvaccinated birds. As vaccinated birds often see a 5-10% decrease in performance during the weeks following vaccination, this is commercially important to poultry producers. The PC1 treated and vaccine challenged birds performed better than the non-vaccinated (non-challenged) birds. The PC1 treated birds continued to segregate, in terms of body weights, throughout the study. By day 14 the Advent +PC1 group was 8% and 13% heavier than the Neg Con and Advent groups respectively.

Experiment 5

Figure 14:
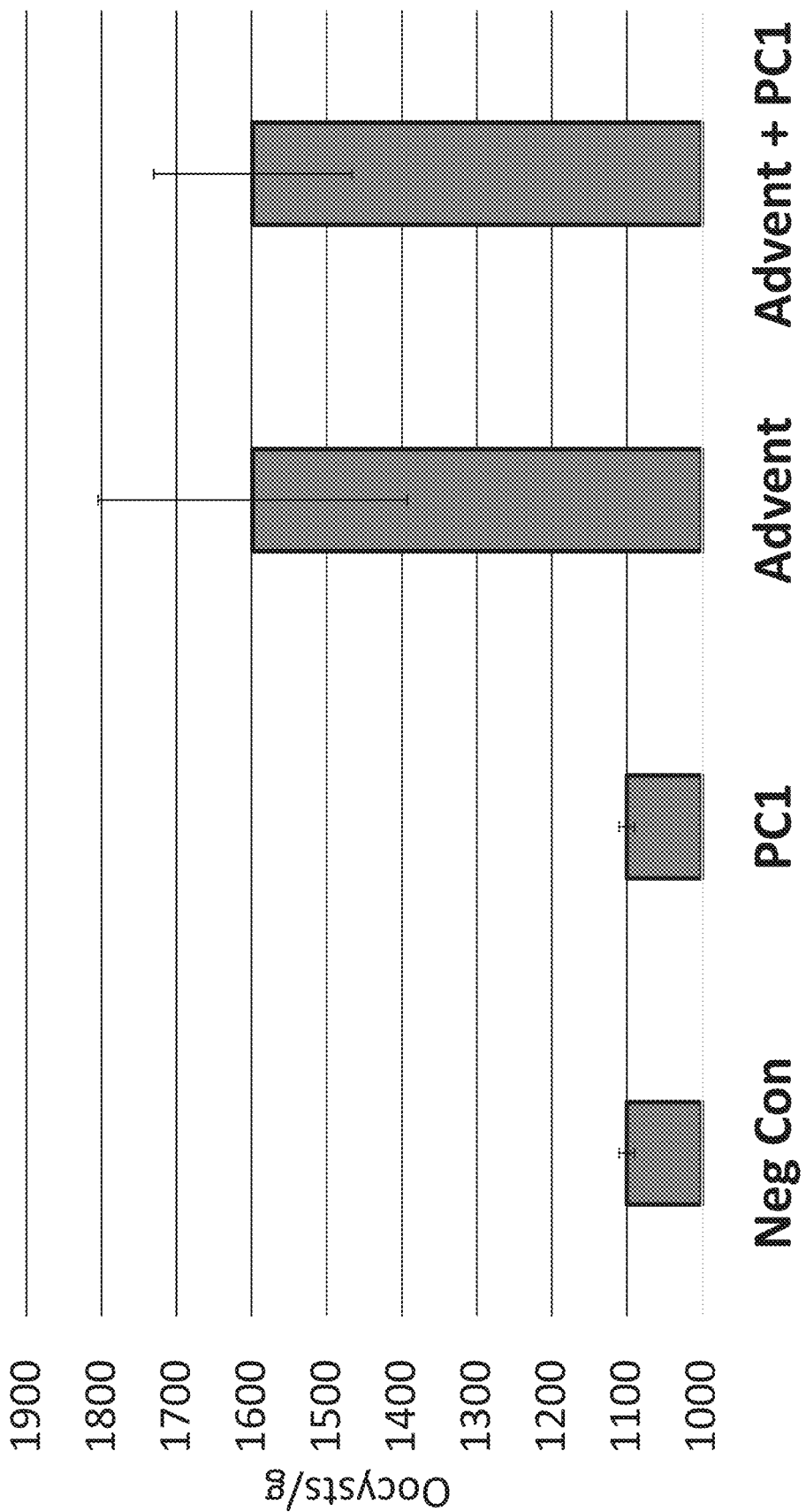
FIG. 14 illustrates oocyst counts on day 7 gut samples, Experiment 5. Saline control (Neg Con), probiotic candidate 1 (PC1), ADVENT® coccidiosis vaccine (Advent), and ADVENT® coccidiosis vaccine and probiotic candidate 1 (Advent+PC1). No significant difference was observed between groups.

Day-of-age hatch chicks were weighed and given $1 \times 10^6$ of probiotic isolates via oral gavage along with a commercially available *Eimeria* vaccine ADVENT® coccidiosis vaccine The objective of this experiment was to demonstrate that chicks vaccinated for coccidiosis and then treated with PC1 do not see a reduction in oocyst cycling, which is important for proper immune response. Chicks were placed on fresh bedding, in block-randomized pens. Chicks were provided a chick starter ration and water. On Day 7, gut samples were collected and lesion scores and oocyst counts (FIG. 14, saline (Neg Con), probiotic candidate 1 (PC1), ADVENT® coccidiosis vaccine (Advent), ADVENT® coccidiosis vaccine and probiotic candidate 1 (Advent +PC1)) were obtained. Lesion scores were minimal with no significant differences observed between groups. These results indicate that it is unlikely that oocyst cycling of the vaccine strains of *Eimeria* are effected by PC1.

Administration of a selected probiotic with a commercial coccidiosis vaccine increased body weight gain, improved flock uniformity and increased villus length in neonatal chicks. Growth, mortality rates and feed conversion of a probiotic formulation may be tested. Long term effects on gut health and microflora populations may be tested. The probiotic formulations may be tested to determine immunomodulatory effects. The above results indicate that PC1 can reduce the deleterious effects often seen with *Eimeria* (coccidiosis) vaccines.

The present disclosure sets forth exemplary isolates, isolate selection criteria, and methods for reducing adverse effects associated with various coccidiosis vaccines. It may be understood that the foregoing description is of exemplary embodiments of the invention, and that the invention is not limited to the specific forms shown. Various modifications may be made in the design and arrangement of the elements set forth herein without departing from the scope of the invention. For example, the various components and devices can be connected together in various manners in addition to those illustrated in the exemplary embodiments, and the various steps can be conducted in different orders. These and other changes or modifications are intended to be included within the scope of the disclosure.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the inventions. The scope of the inventions is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Systems, methods and apparatus are provided herein. In the detailed description herein, references to "one embodiment", "an embodiment", "various embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

The invention claimed is:

1. A method for reducing an adverse effect associated with a coccidiosis vaccine in a poultry, comprising co-administering a single dose of bacterium *Lactobacillus salivarius* or *Pediococcus pentosaceus* and of a coccidiosis vaccine to the poultry, wherein the bacterium reduces or prevents at least one adverse effect associated with the coccidiosis vaccine.

2. The method of claim 1, wherein the bacterium and the coccidiosis vaccine are administered simultaneously.

3. The method of claim 1, wherein the bacterium and the coccidiosis vaccine are administered within 1 second of each other.

4. The method of claim 1, wherein the bacterium and the coccidiosis vaccine are administered within 10 seconds of each other.

5. The method of claim 1, wherein the bacterium and the coccidiosis vaccine are administered within 1 minute of each other.

6. The method of claim 1, wherein the bacterium and the coccidiosis vaccine are administered within 10 minutes of each other.

7. The method of claim 1, wherein the bacterium and the coccidiosis vaccine are administered within 1 hour of each other.

8. The method of claim 1, wherein the bacterium and the coccidiosis vaccine are administered within 10 hours of each other.

9. The method of claim 1, wherein the bacterium and the coccidiosis vaccine are administered within 1 day of each other.

10. The method of claim 1, wherein the adverse effect comprises at least one of an inflammatory condition and a secondary infection.

11. The method of claim 10, wherein the secondary infection is caused by at least one of *Clostridium perfringens*, *Escherichia coli*, and *Salmonella enterica*.

12. The method of claim 1, wherein the bacterium does not substantially reduce the effectiveness of the coccidiosis vaccine.

13. The method of claim 1, wherein the bacterium is administered by one of a food source, water, oral gavage, and aerosol spray.

14. The method of claim 1, wherein the bacterium improves the intestinal morphology of the gastrointestinal tract of the poultry.

15. The method of claim 1, wherein the bacterium reduces the level of a bio-marker associated with inflammation of a poultry gastrointestinal tract.

16. The method of claim 15, wherein the bio-marker is an alpha-1 glycoprotein.

17. The method of claim 1, wherein the bacterium affects the time of food passage in the poultry.

18. The method of claim 1, wherein the bacterium comprises a bacterium selected from the gastrointestinal tract of the poultry.

* * * * *